United States Patent
Baserga et al.

(10) Patent No.: US 6,340,674 B1
(45) Date of Patent: Jan. 22, 2002

(54) METHOD OF INHIBITING THE PROLIFERATION AND CAUSING THE DIFFERENTIATION OF CELLS WITH IGF-1 RECEPTOR ANTISENSE OLIGONUCLEOTIDES

(75) Inventors: Renato Baserga, Ardmore; Christian Sell, Philadelphia; Raphael Rubin, Penn Valley, all of PA (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 09/668,822

(22) Filed: Sep. 22, 2000

Related U.S. Application Data

(63) Continuation of application No. 08/880,313, filed on Jun. 20, 1997, which is a continuation of application No. 08/479,173, filed on Jun. 6, 1995, now Pat. No. 5,643,788, which is a continuation of application No. 08/158,176, filed on Nov. 23, 1993, now Pat. No. 5,456,612, which is a continuation-in-part of application No. 08/037,257, filed on Mar. 26, 1993, now abandoned.

(51) Int. Cl.$^7$ .................... A61K 48/00; C07H 21/04; C12N 15/09

(52) U.S. Cl. .................... 514/44; 536/24.5; 536/24.1; 536/23.1; 435/455; 435/377; 435/375

(58) Field of Search ................ 536/23.1, 24.1, 536/24.5; 514/44; 435/455, 375, 377

(56) References Cited

U.S. PATENT DOCUMENTS

| | | |
|---|---|---|
| 4,736,866 A | 4/1988 | Leder et al. |
| 4,873,191 A | 10/1989 | Wagner et al. |
| 5,077,059 A | 12/1991 | Mishima et al. |
| 5,139,941 A | 8/1992 | Muzyczka et al. |
| 5,173,414 A | 12/1992 | Lebkowski et al. |
| 5,252,479 A | 10/1993 | Srivastava |
| 5,262,308 A | 11/1993 | Baserga |
| 5,271,941 A | 12/1993 | Cho-chung |
| 5,272,082 A | 12/1993 | Santoli et al. |
| 5,354,674 A | 10/1994 | Hodgson |
| 5,354,678 A | 10/1994 | Lebkowski et al. |
| 5,399,346 A | 3/1995 | Anderson et al. |
| 5,460,831 A | 10/1995 | Kossovsky et al. |

FOREIGN PATENT DOCUMENTS

| | | |
|---|---|---|
| WO | WO 91/17253 | 11/1991 |
| WO | WO 93/20691 | 10/1993 |
| WO | WO 92/22486 | 10/1994 |
| WO | WO 94/23034 | 10/1994 |
| WO | WO 96/14746 | 5/1996 |
| WO | WO 97/18241 | 5/1997 |
| WO | WO 97/37010 | 10/1997 |
| WO | WO 99/23259 | 5/1999 |

OTHER PUBLICATIONS

Douglas W. Green, et al., Antisense Oligonucleotides: An Evolving Technology for the Modulation of Gene Expression in Human Disease, Jul. 2000, American College of Surgeons, pp. 93–105.*

Andrea D. Branch, A Good Antisense Molecule is Hard to Find, Feb. 1998, TIBS vol. 23, pp. 45–50.*

Agrawal et al., "Antisense Oligonucleotide Based Therapeutic Approach: From Laboratory to Clinical Trials," *Antisense Therapy: Efficacy and Delivery of Antisense & Ribozine Oligonucleotide* (Feb. 23–25, 1995 London).

Arad et al., "Use of reconstructed Sendai virus envelopes for fusion–mediated microinjection of double–stranded RNA," *Biochem. Biophy. Acta.*, 1986, vol. 859, pp. 88–94.

Baker et al., "Role of Insulin–like Growth Factors in Embryonic and Postnatal Growth," *Cell*, 1993, vol. 75, pp. 73–82.

Baserga, The Insulin–like Growth Factor I Receptor: A Key to Tumor Growth?, *Cancer Research*, 1995, vol. 55, pp. 249–252.

Baserga and Rubin, "Cell Cycle and Growth Control," *Critical Reviews in Eukaryote Gene Expression*, 1993, vol. 3, pp. 47–61.

Bayever et al., "Oligonucleotides in the Treatment of Leukemia," *Hematological Oncology*, 1994, vol. 12, pp. 9–14.

Becker et al., "Proliferation of Human Malignant Melanomas is inhibited by Antisense Oliodeoxynucleotides targeted against basic fibroblast growth factor", *The Embo Jour.*, 1989, vol. 8, pp. 3685–3691.

Brown, D., "Gene therapy "oversold" by researchers, Journalists," *Washington Post*, 1995, A1 + A22.

Chomczynski and Sacchi, "Single–Step Method of RNA Isolation by Acid Guanidinium Thiocyanate–Phenol–Chloroform Extraction," *Anal. Biochem.*,1987, vol. 162, pp. 156–159.

Coghlan, A., *New Scientist*, 1995, pp. 14–15.

Craig et al., "Sequence Organization of Two Recombinant Plasmids Containing Genes for the Major Heat Shock–induced Protein of *D. melanogaster,*" *Cell*, 1979, vol. 16, pp. 575.

Culver, K. et al., TIG, 1994, vol. 10, #5, pp. 174–178.

(List continued on next page.)

*Primary Examiner*—Sean McGarry
(74) *Attorney, Agent, or Firm*—Woodcock Washburn Kurtz Mackiewicz & Norris LLP

(57) ABSTRACT

A method of inhibiting the proliferation and causing the differentiation of undifferentiated cells comprising contacting the undifferentiated cells with an effective amount of an antisense oligonucleotide having a sequence which is complementary to a region of the IGF-1 receptor RNA. The sequence of the antisense oligonucleotide is selected from an oligodeoxynucleotide sequence complementary to codons −29 to −24 of the signal sequence of the IGF-1 receptor and an oligoribodeoxynucleotide sequence complementary to codons 1 to 309 of the sequence of the IGF-1 receptor. The oligoribonucleotide sequence may be provided by an expression vector.

26 Claims, 12 Drawing Sheets

OTHER PUBLICATIONS de Fabritis et al., "In vitro Purging with BCR–BRL Antisense Oligonucleotide does not Prevent Haematologic Reconstitution After Autologous Bone Marrow Transplantation," *Leukemia,* 1995, vol. 9(4), pp. 661–664.

Dzav, V., et al., TIBTECH, 1993, vol. 11, pp. 205–210.

Feinberg and Vogelstein, "A Technique for Radiolabeling DNA Restriction Endonuclease Fragments to High Specific Activity," *Anal Biochem.,* 1983, vol. 132, pp. 6–13.

Floros et al., "Induction of Cell DNA Replication in G1–Specific ts Mutants by Microinjection of SV40 DNA," *Exp. Cell Res.,* 1981, vol. 132, pp. 215.

Gennaro, Alfonso, ed., "Remington's Pharmaceutical Sciences," 18th Edition, 1990.

Goldring and Goldring, "Cytokines and Cell Growth Control," *Eukaryote Gene Expression,* 1991, vol. 1, pp. 301–326.

Gritz et al., "Plasmid–encoded hygromycin B resistance: the sequence of hygromycin B phosphotransferase gene and its expression in *Escherichia coli* and *Saccharomyces cerevisiae,*" *Gene,* 1983, vol. 25, pp. 179.

Gura, T. et al., *Science,* 1995, vol. 270, pp. 575–577.

Holt, J. et al., *PNAS,* 1986, vol. 83, pp. 4794–4778.

Jat et al., "Cell lines established by a temperature–sensitive simian virus 40 large–T–antigen gene are growth restricted at the nonpermissive temperature," *Mol. Cell. Biol,* 1989, 9, p. 1672.

Hiija et al., "Biologic and Therapeutic Significance of MYB Expression in Human Melanona," *Proc. Natl. Acad. Sci.,* 1994, vol. 91, pp. 4499–4503.

Hug, P. et al., *Biochem. Biophys. Ana.,* 1991, vol. 1097, pp. 1–17.

Jat et al., "Cell Lines Established by a Temperature–Sensitive Simian Virus 40 Large–T–Antigen Gene Are Growth Restricted at the Nonpermissive Temperature," *Mol. Cell. Biol.,* 1989, vol. 9, pp. 1672.

Kaleko et al., "Overexpression of the Human Insulinlike Growth Factor I Receptor Promotes ligand–Dependent Neoplastic Transformation," *Mol. Cell. Biol.,* 1990, vol. 10, pp. 464–473.

Lammers et al., "Differential signalling potential of insulin–and IFG–1–receptor cytoplasmic domains," *EMBO J.,* 1989, vol. 8, pp. 1369–1375.

Lipson et al., "Transcriptional activity of the human thymidine kinase gene determined by a method using the polymerase chain reaction and an intron–specific probe," *Proc. Natl. Acad. Sci. U.S.A.,* 1989, vol. 86, pp. 9774–9777.

Liu et al., "Mice Carrying Null Mutations of the Genes Encoding Insulin–like kGrowth Factor 1 (igf–1) and Type 1 IGF Receptor (ifglr)," *Cell,* 1993, vol. 75, pp. 59–72.

Loke, S. et al., "Cancer Topics in Microbiol. And Immunol.," 1988, vol. 141, pp. 282–289.

Long et al., Loss of the Mestatatic Phenotype in Murine Carcinoma Cells Expressing an Antisense RNA to the Insulin–like Growth Factor Receptor, *Cancer Research,* 1995, vol. 55, pp. 1006–1009.

Macaulay, "Insulin–like growth factors and cancer," *Br. J. Cancer,* 1992, vol. 65, pp. 311–320.

Marks, J. et al., *M–1 Endocrinal,* 1991, vol. 5 (8), pp. 1158–1168.

Marola, D. et al., Biochem Biophys. Res. Comm., 1987, vol. 147, pp. 288–194.

McCubrey, et al., "Growth–Promoting Effects of Insulin––like Growth Factor–1 (IGF–1) on Hematopoietic Cells," *Blood,* 1991, vol. 78, pp. 921–929.

Nabel et al., "Direct Gene Transfer with DNA–Liposome Complexes in Melanona: Expression, Biologic Activity, and Lack of Toxicity in Humans," *Proc. Natl. Acad. Sci.,* 1993, vol. 90, pp. 11307–11311.

Pietrzkowski et al., "Inhibition of Growth of Prostatic Cancer Cell Lines by Peptide Analogues of Insulin–like Growth Factor 1," *Cancer Res.,* 1993, vol. 53, pp. 1102–1106.

Pietrzkowski et al., "Constitutive Expression of Insulin–like Growth Factor 1 and Insulin–like Growth Factor–1 Receptor Abrogates All Requirements for Exogenous Growth Factors[1],*"* *Cell Growth & Diff.,* 1992, vol. 3, pp. 199–205.

Pietrzkowski et al., "Roles of Insulinlike Growth Factor 1 (IGF–1) and the IGF–1 Receptor in Epidermal Growth Factor–Stimulated Growth of 3T3 Cells," *Mol. Cell. Biol.,* 1992, vol. 12, pp. 3883–3889.

Pietrzkowski et al., "Inhibition of Cellular Proliferation by Peptide Analogues of Insulin–Like Growth Factors," *Cancer Res.,* 1992, pp. 6447–6451.

Porcu et al., "The Growth–Stimulatory Effect of Simian Virus 40 T Antigen Requires the Interaction of Insulinlike Growth Factor 1 with Its Receptor," *Mol. Cell. Biol.,* 1992, vol. 12, pp. 5069–5077.

Radna et al., "Growth of Immorta Simian Virus 40 tsA––Transformed Human Fibroblasts is Temperature Dependent," *Mol. Cell. Biol.,* 1989, vol. 9, pp. 3093.

Rappolee, et al., "Novel method for studying mRNA phenotypes in single or small numbers of cells," *J. Cell. Biochem.,* 1989, 39, 1–11.

Ratajczak et al., "Oligonucleotide Therapeutics for Human Leukemia Antisense Therapy; Efficacy and Delivery of Antisense & Ribozome Oligonucleotide," (presented Feb. 23–24, 1995, London).

Reiss et al., "The insulin–like growth factor 1 receptor is required for the proliferation of hemopoiectic cells," *Oncogene,* 1992, vol. 7, pp. 2243–2248.

Resnick–Silverman et al., "Retinoblastoma Protein and Simian Virus 40–Dependent Immortalization of Human Fibroblasts," *J. Virol.,* 1991, vol. 65, pp. 2845.

Resnicoff et al., "Growth Inhibition of Human Melanoma Cells in Nude Mice by Antisense Strategies to the Type I Insulin–like Growth Factor Receptor[1],*"* *Cancer Research,* 1994, vol. 54, pp. 4848–4850.

Resnicoff et al., "The Insulin–like Growth Factor i Receptor Protects Tumor Cells from Apoptosis in Vivo[1],*"* *Cancer Research,* 1995, vol. 55, pp. 2463–2469.

Sell et al., "Simian Virus 40 Large Tumor Antigen is unable to transform mouse embryonic fibrobasts lacking type 1 insulin–like growth factor receptor", *PNAS,* 1993, vol. 90, pp. 11217–11221.

Shen et al., "Gene Transfer: DNA Microinjection Compared with DNA Transfection with a Very High Efficiency," *Mol. Cell. Biol.,* 1982, vol. 2, pp 1145.

Stein, C. et al., Science, 1993, vol. 261, pp. 1004–1012.

Stein, G.H., "T98G: An Anchorage–independent Human Tumor Cell Line that Exhibits Stationary Phase G1 Arrest in Vitro," *J. Cell. Physiol.,* 1979, vol. 99, pp. 43.

Talavera et al., "Insulin–like Growth Factor 1 Receptors in Normal and Neoplastic Human Endometrium", *Cancer Res.,* 1990, vol. 50, pp. 3019–3024.

Tegtmeyer, "Function of Simian Virus 40 Gene A in Transforming Infection," *J. Virol.,* 1975, vol. 15, pp. 613.

Todaro et al., "Quantitative Studies of the Growth of Mouse Embryo Cells in Culture and Their Development Into Established Lines," *J. Cell Biol.*, 1963, vol. 17, pp. 299.

Trojan et al., "Treatment and Prevention of Rat Glioblastoma by Immunogenic C6 Cells Expressing Antisense Insulin–Like Growth Factor 1 RNA," *Science*, 1993, vol. 259, pp. 94–97.

Thomas, P.S., "Hybridization of Denatured RNA Transferred or Dotted to Nitrocellulose Paper," *Methods Enzymol.*, 1983, vol. 100, pp. 255–266.

Thompson et al., "Dissociation of Rb–Binding and Anchorage–Independent Growth From Immortalization and Tumorigenicity Using SV40 Mutants Producing N–Terminally Truncated Large T Antigens," *Virology*, 1990, vol. 178, pp. 15.

Trojan et al., "Loss of tumorigenicity of rat glioblastoma directed by episome–based antisense cDNA transcription of insulin–like growth factor I," *Proc. Natl. Acad. Sci. U.S.A.*, 1992, vol. 89, pp. 4874–4878.

Trojan, J., *J. Cell Biology*, 1991, vol. 115 (3, pt. 2), pp. 263a.

Tseng, B. et al., "Antisense oligonucleotide technology in the development of cancer therapeutics," Cancer Gene Therapy, 1994, vol. 1, pp. 65–71.

Uhlmann et al., "Antisense Oligonucleotides: A New Therapeutic Principle Chemical Reviews", *Amer. Chemical Soc.*, 1990.

Ullrich et al., "Insulin–like growth factor I receptor primary structure," *EMBO J.*, 1986, vol. 5, pp. 2503–2512.

Warton et al., "Growth and maintenance of BALB/c–3T3 cells," *Cell Growth and Division*, 1989, pp. 139–153.

Weiss, R., Science News, 1991, vol. 139, pp. 108–109.

Wetmur, J., "DNA probes: applications of the principles of nucleic acid hybridization," Crit. Rev. Biochem., *Mol. Biol.*, 1991, vol. 26 (3/4), pp. 227–259.

Wickstrom et al., "Antisense DNA Methylphosphonate Inhibition of C–MYC Gene Expression in Transgenic Mice", 75th. *Ann Mtg. Fed. Of Amer. Soc. for Experimental Biology*, 1991.

Yamori et al., "Insulin–like Growth Factor I Rapidly Induces Tyrosine Phosphorylation of a $M_r$ 150,000 and a $M_r$ 160,000 Protein in Highly Metastatic Mouse Colon Carcinoma 26 ML–17 Cells$_1$", *Cancer Res.*, 1991, vol. 51, pp. 5859.

Abraham et al., "Survival and Development of larval *Onchocerca Volvulus* in Diffusion Chambers Implanted in Primate and Rodent Hosts", *J. Parasitol.*, 1993, 79, 571–582.

Barry, M. et al., "Activation of Programmed Cell Death (Apoptosis) by Cisplatin, Other Anticancer Drugs, Toxins and Hyperthermia", *Biochem. Pharmacol.*, 1990, 40, 2353–2362.

Baserga, R., "Oncogenes and the Strategy of Growth Factors", *Cell*, 1994, 79, 927–930.

Bursch, W. et al., "Determination of the length of the histological stage of apoptosis in normal liver and in altered hepatic foci of rats", *Carcinogenesis*, 1990, 11, 847–853.

Buttyan, R. et al., "Induction of the TRPM–2 Gene in Cells Undergoing Programmed Death", *Mol. Cell. Biol.*, 1989, 9, 3473–3481.

Coppola, D. et al., "A Functional Insulin–Like Growth Factor I Receptor Is Required for the Mitogenic and Transforming Activities of the Epidermal Growth Factor Receptor", *Mol. Cell. Biol.*, 1994, 14, 4588–4595.

Lange, A.M. et al., "IL–4–and IL–5–Dependent Protective Immunity to Onchocerca volvulus Infective Larvae in BALB/BYj mice[1]", *Immunol.*, 1994, 153, 205–211.

Lanza, R.P. et al., "Xenogeneic Humoral Responses to Islets Transplanted in Biohybrid Diffusion Chambers", *Transplantation*, 1994, 57, 1371–1375.

Preston, G.A. et al., "Regulation of Apoptosis by Low Serum in Cells of Different Stages of Neoplastic Progression: Enhanced Susceptibility after Loss of a Senescence Gene and Decreased Susceptibility after Loss of a Tumor Suppressor Gene", *Cancer Res.*, 1994, 54, 4214–4223.

Resnicoff, M. et al., "Correlation between Apoptosis, Tumorigenesis, and Levels of Insulin–like Growth Factor I Receptors", *Cancer Res.*, 1995, 55, 3739–3741.

Scher, C.D. et al., "Platelet–Derived Growth Factor and the Regulation of the Mammalian Fibroblast Cell Cycle", *Biochem. Biophys. Acta.*, 1979, 560, 217–241.

Stiles, C.D. et al., "Dual control of cell growth by somatomedins and platelet–derived growth factor", *Proc. Natl. Acad. Sci. USA*, 1979, 76, 1279–1283.

Ullrich, A. et al., "Signal Transduction by Receptors with Tyrosine Kinase Activity", *Cell*, 1990, 61, 203–212.

Zhou–Li, F. et al., "Association of Insulin Receptor Substrate 1 with Simian Virus 40 Large T Antigen", *Mol. Cell Biol.*, 1995, 15, 4232–4239.

Martin et al., "Development of an in vitro Assay for the Survival of Cells Suspended from BA1112 Rat Sarcomas", *Eur. J. Cancer Clin. Oncol.*, 1983, 19(6), 791–797.

Lahm, H. et al., "Growth Inhibition of Human Colorectal Carcinomas by a Monoclonal Antibody Directed Against the IGF–1 Receptor," *Eur. J. Cancer*, 1991, 27(Suppl. 3), Abstract No. 11.053.

Pietrzykowski, Z. et al., "Autocrine Growth of Cells Overexpressing the Human IGF–1 and IGF–1 Receptor Genes," *Federal of American Society for Experimental Biology*, 75th Annual Meeting, Atlanta, GA, 1991, Part 3, Abstract No. 7268.

Wickstrom, E. et al., "Antisense DNA Methylphosphonate Inhibition of C–MYC Gene Expression in Transgenic Mice," *FASEB J.*, 75th Annual Meeting, Atlanta, GA, 1991, Part 2, Abstract No. 6218.

Rohlik, et al., "An antibody to the receptor for insulin–like growth factor I inhibits the growth of MCF-7 cells in tissue culture," *Biochem. Biophys. Res. Comm.*, 1987, 149, 276–281.

Resnicoff, M., et al., "Regression of C6 rat brain tumors by cells expressing an antisense insulin–like growth factor I receptor RNA," *J. Exp. Therap. Oncol.*, 1996, 1, 385–389.

Arteaga, C.L., "Interference of the IGF system as a strategy to inhibit breast cancer growth", *Breast Canc. Res. Treat.*, 1992, 22, 101–106.

Baserga, R., "Controlling IGF–receptor function: a possible strategy for tumor therapy", *Trends in Biotech.*, 1996, 14, 150–152.

Campbell, P.G. et al., "Insulin–like growth factor binding protein (IGFBP) inhibits IGF action on human osteosarcoma cells", *J. Cell. Physiol.*, 1991, 149, 293–300.

Christofori, G. et al., "A second signal supplied by insulin–like growth factor II in oncogene–induced tumorigenesis", *Nature*, 1994, 369, 414–418.

DiAmbrosio, C. et al., "A Soluble Insulin–like Growth Factor I Receptor That Induces Apoptosis of Tumor Cells in Vivo and Inhibits Tumorigenesis", *Cancer Res.*, 1996, 56, 4013–4020.

Kalebic, T. et al., "In Vivo Treatment with Antibody against IGF–1 Receptor Suppresses Growth of Human Rhabdomyosarcoma and Down–Regulates p34[cdc2]", Cancer Res., 1994, 54, 5531–5534.

Kauffman, S., "Induction of Endonucleolytic DNA Cleavage in Human Acute Myelogenous Leukemia Cells by Etoposide, Camptothecin, and other Cytotoxic Anticancer Drugs: A Cautionary Note[1]", Cancer Res., 1989, 49, 5870–5878.

Li, S. et al., "Mitogenicity and Transforming Activity of the Insulin–like Growth Factor–I Receptor with Mutations in the Tyrosine Kinase Domain", J. Biol. Chem., 1994, 269, 32558–32564.

Miura, M. et al., "Effect of a Mutation at Tyrosine 950 of the Insulin–like Growth Factor Receptor on the Growth and Transformation of Cells[1]", Cancer Res., 1995, 55, 663–667.

Baserga and Rubin, "Cell Cycle and Growth Control", Crit. Rev. Eukaryot. Gene Expr., 1993, 3, 47–61.

Conley, "Transplantation of nervous system tumors in diffusion chambers", J. Neurosurg., 1974, 41, 332–338.

Harrington et al., "c–Myc–induced apoptosis in fibroblasts is inhibited by specific cytokines", EMBO J., 1994, 13, 3286–3295.

Kaufmann, S.H., "Induction of Endonucleolytic DNA Cleavage in Human Acute Myelogenous Leukemia Cells by Etoposide, Camptothecin, and Other Cytotoxic Anticancer Drugs: A Cautionary Note", Cancer Res., 1989, 49, 5870–5878.

Kolata, "In the rush toward gene therapy, some see a high risk of failure", The New York Times, Jul. 25, 1995, p. C3.

Marshall, "Gene Therapy's Growing Pains", Science, 1995, 269, 1050–1055.

Ray et al., "Ca2+ antagonists inhibit DNA fragmentation and toxic cell death induced by acetaminophen", FASEB J., 1993, 7, 453–463.

Wu–Pong, "Oligonucleotides: Opportunities for Drug Therapy and Research", Pharm. Tech., 1994, 102, 104, 106, 108, 110–112, and 114.

Cox et al., "Identification of a Peptide Recognized by Five Melanoma–Specific Human Cytotoxic T Cell Lines", Science, 1994, 264, 716–719.

D'Ambrosio et al., "A Soluble Insulin–like Growth Factor I Receptor That Induces Apoptosis for Tumor Cells in vivo and Inhibits Tumorigenesis", Cancer Res., 1996, 56, 4013–4020.

Kawakami et al., "Identification of a human melanoma antigen recognized by tumor–infiltrating lymphocytes associated with in vivo tumor rejection", Proc. Natl. Acad. Sci. USA, 1994, 91, 6458–6462.

Miller et al., "Gene Transfer and Antisense Nucleic Acid Techniques", Parasitology Today, 1994, 10(3), 92–97.

Valentinis et al., "The role of the insulin–like growth factor I receptor in the transformation by simian virus 40 T antigen", Oncogene, 1994, 9, 825–831.

Rogler, C.E. et al., "Altered Body Composition and Increased Frequency of Diverse Malignancies in Insulin–Like Growth Factor II Transgenic Mice", J. Biol. Chem., 1994, 269, 13779–13784.

Sell, C. et al., "Insulin–like Growth Factor I (IGF–1) and the IGF–1 Receptor Prevent Etoposide–induced Apoptosis[1]", Cancer Res., 1995, 55, 303–306.

Shapiro, D.N. et al, "Antisense–mediated Reduction in Insulin–like Growth Factor–1 Receptor Expression Suppresses the Malignant Phenotype of a Human Alveolar Rhabdomyosarcoma", J. Clin. Invest., 1994, 94, 1235–1242.

Surmacz, E. et al., "Dissociation of Mitogenesis and Transforming Activity by C–Terminal Truncation of the Insulin–like Growth Factor–1 Receptor", Exp. Cell. Res., 1995, 218, 370–380.

Prager, D. et al., "Dominant negative inhibition of tumorigenesis in vivo by human insulin growth factor I receptor mutant", Proc. Natl. Acad. Sci. USA, 1994, 91, 2181–2185.

Shapiro, D. N. et al., "Antisense–mediated reduction in insulin–like growth factor–1 receptor expression suppresses the malignant phenotype of a human rhabdomyosarcoma," Cancer Res., Eighty–Third Annual Meeting, 1992, 33, Abstract No. 2112.

Yamasaki, H. et al., "Human Insulin–like Growth Factor I Receptor [950] Tyrosine Is Required for Somatotroph Growth Factor Signal Tranduction," J. Biol. Chem., 1992, 267(29), 20953–20958.

Yamasaki, H. et al., "Structure–Function of the Human Insulin–Like Growth Factor–I Receptor: A Discordance of Somatotroph Internalization and Signaling," Mol. Endocrinology, 1993, 7, 681–685.

Yamasaki, H. et al., "Binding and Action of Insulin–Like Growth Factor I in Pituitary Tumor Cells," Endocrinology, 1991, 128(2), 857–862.

Milligan, et al., J. Med. Chem., 1993, 36(14), 1923–1937.

Westermann, et al., Biomed. Biochem. Acta, 1989, 48, 85–93.

Mercola, et al., Biochem. And Biophys. Res. Commun., 1987, 147(1), 288–294.

Pietrzkowski, Z., et al., "Autocrine growth of cells overexpressing the human IGF–1 and IGF–1 receptor genes," FASEB, 1991, Part 3, Abstract 7268.

Agrawal, S., "Antisense Oligonucleotides: Towards clinical trials," TIBTECH, 1996, 14, 376–387.

Restifo, et al., J. Immunother, 1993, 14, 182–190.

Branch, Antisense & Nucleic Acid Drug Dev., 1998, 8, 249–254.

James, Antiviral Chemistry & Chemotherapy, 1991, 2(4), 191–214.

Vogelstein, et al., Trends in Genetics, 1993, 9(4), 139–142.

Resnicoff, M., et al., "Antitumor effects elicited by antisense–mediated downregulation of the insulin–like growth factor I receptor (Review)," Int. J. Mol. Med., 1998, 883–888.

Resnicoff, M., et al., "Antitumor effects elicited by antisense–medicated downregulation of the IGF–1 receptor: From the bench to the bedside," Proceedings of the American Association for Cancer Research Annual Meeting, 1999, vol. 40, 729, Abstract No. 4816.

Hoelzer, D. et al., "Low–dose Ara–C in the Treatment of Acute Leukemia Cytotoxicity or Differentiation Induction," Blut, 1984, 48(4), 233–238.

Huybrechts, M. et al., "The Diffusion Chamber Technique as an in Vivo Assay in Mice for the Effectiveness of Antitumor Agents," Scand. J. Haem., 1979, 23(3), 223–226.

Lavin, M.F. et al., "Role of protein kinase activity in apoptosis," Experientia, 1996, 52(10–11), 979–994.

Lieberthal, W. et al., "Mechanisms of apoptosis and its potential role in renal tubular epithelial cell injury," Am. Physiol. Soc., 1996, 271(3 Part 2), F477–F488.

Wharton, et al., Cell Growth and Division, 1989, 10, 139–153.

* cited by examiner

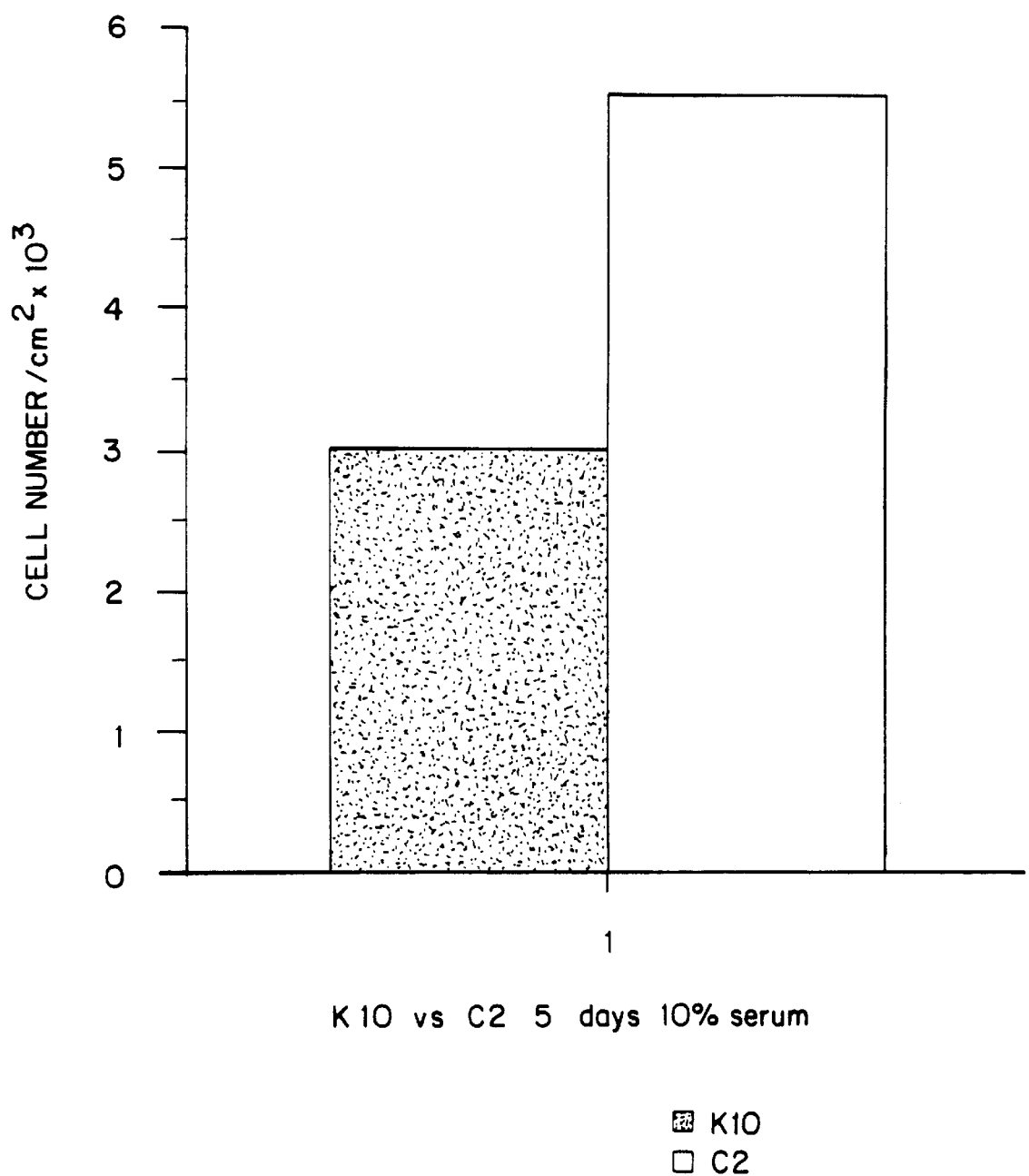

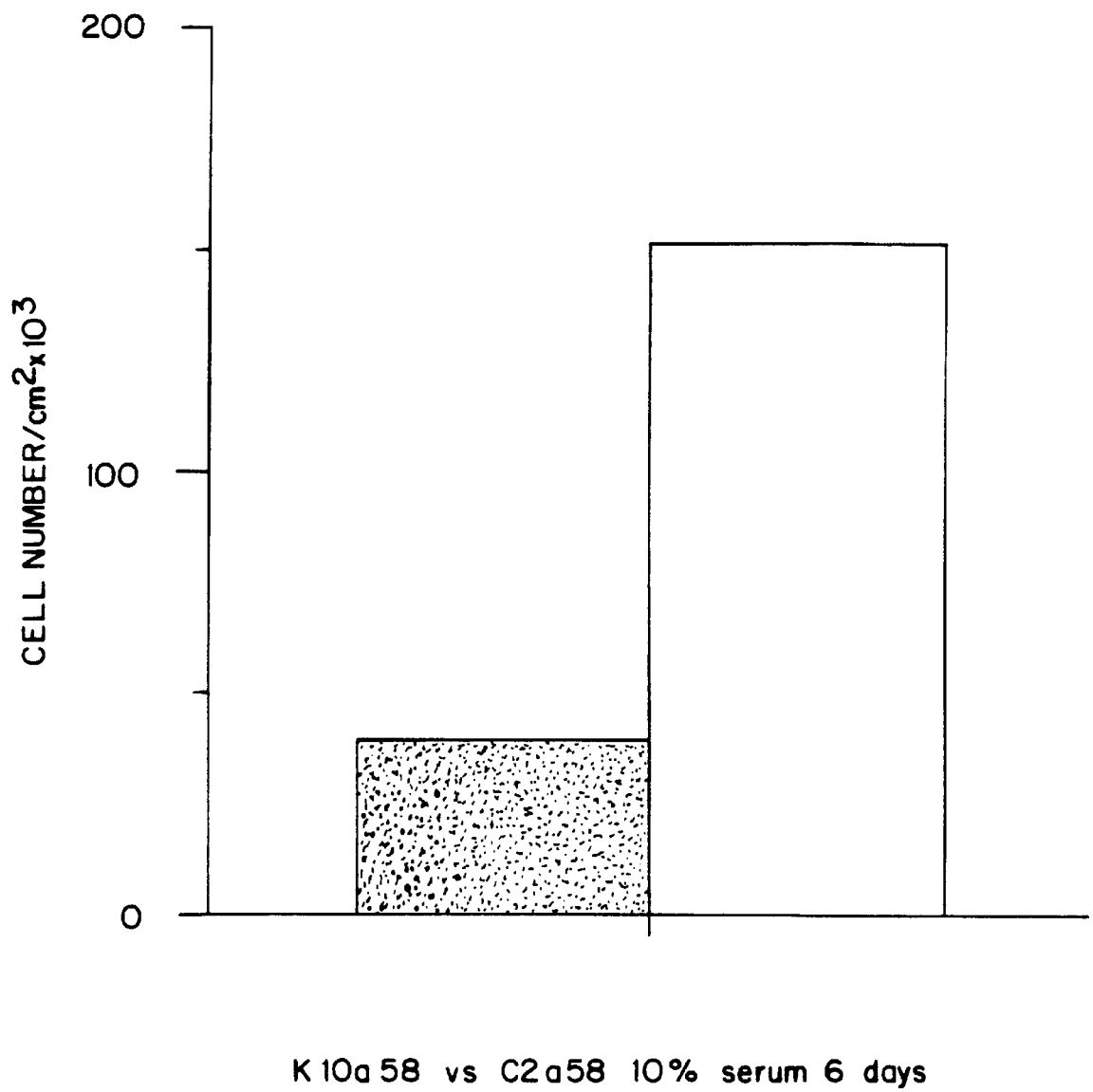

TTTTTTTTTTTGAGAAAGGGAATTTCATCCCAAATAAAAGGATGAAGTCTGGCTCCGGAGAGGGTCCCG

-30
MetLysSerGlyGlyGlySerPro
-20                                           -10                                                    -1 1         α subunit
ThrSerLeuTrpGlyLeuLeuPheLeuSerLeuAlaAlaLeuSerLeuTrpProThrSerGlyGluValIle CysGlyPro
ACCTCGCTGTGGGGGCTCCTGTTTCTCTCCGCTGCGCTCTCGCTCTGGCCGACGAGTGGAGAAATCTGGGCCA                          150

10                                         20                                        30
GlyIleAspIleArgAsnAspTyrGlnGlnLeuLysArgGlnLeuGluAsn CysThrValIleGluGlyTyrLeuHis
GGCATCGACATCCGCAACGACTATCAGCAGCTGAAGCGCCTGGAGAACTGCACGGTGATCGAGGGCTACCTCCAC 40                                         50
IleLeuLeuIleSerLysSerAlaGluAspAspTyrArgArgSerTyrArgPheProLysLeuThrValIleThrGluTyrLeu
ATCCTGCTCATCTCCAAGGCCGAGGACGACTACCGGCGCAGCTACCGCTTCCCCAAGCTCACGGTCATCACCGAGTACTTG    300

60                                         70                                         80
LeuPheArgValAlaGlyLeuLeuGluSerLeuGlyAspAspLeuValIleArgGlyTyrLeuAsnLeuArgAsn
CTGTTCCGAGTGGCCCTCCTGGAGAGCCTCGGAGACGACCTGGTCATCCGGGGCTACCTGAAC 90                                        100
LeuPheTyrAsnTyrAlaLeuValIlePheGluMetThrAsnLeuLysAspIleIleGlyIleGlyLeuTyrAsnLeuArgAsn
CTCTTCTACAACTACGCCCTGGTCATCTTCGAGATGACCAATCTCAAGGATATTGGGCTTTACAACCTGAGGAAC    450

110                                        120                                       130
IleThrArgGlyAlaIleLeuArgIleGluLysGluAspLeuCysTyrLeuSerThrValAspTrpSerLeuIle
ATTACTCGGGGGGCCATCCTCAGGATTGAGAAAGAAGATCTGTGCTACCTCTCCACTGTGGACTGGTCCCTGATC 140                                       150
LeuAspAlaValSerAsnAsnTyrIleValGlyAsnLysProProLysGluCysGlyAspLeuCysProGlyThr
CTGGATGCGGTGTCCAATAACTACATTGTGGGGAATAAGCCCCCAAAGGAATGTGGGGACCTGTGTCCAGGGACC   600

160                                       170                                       180
MetGluGluLysProMet CysGluGluLysThrThrIleAsnAsnGluTyrArg CysTrpThrThrAsnArg
ATGGAGGAGAAGCCGATGTGTGAGGAAAAGACCACCATCAACAATGAGTACAGGTGCTGGACCACAAACCGC

FIG. 7A

CysGlnLysMetCysProSerThrCysGlyLysArgAlaCysThrGluAsnAsnGluCysCysHisProGluCys
TGCCAGAAAATGTGCCCAAGCACGTGCGGGAAGCGGTGCACCGAGAACAATGAGTGCTGCCACCCCGAGTGC

LeuGlySerCysSerAlaProAspAsnAspThrAlaCysValAlaCysArgHisTyrTyrAlaGlyValCys
CTGGGCAGCTGCAGCGCGCCTGACAACGACACGGCCTGTGTAGCTTGCCGCCACTACTATGCCGGTGTCTGT

ValProAlaCysProProAsnThrTyrArgPheGluGlyTrpArgCysValAspArgAspPheCysAlaAsnIle
GTGCCTGCCTGCCCGCGCCCCAACACCTACAGGTTTGAGGGCTGGCGCTGTGTGGACCGTGACTTCTGCGCCAACATC

LeuSerAlaGluSerSerAspSerGluGlyPheValIleHisAspGlyGluCysMetGlnGluCysProSerGly
CTCAGCGCGGAGAGCAGCGACTCCGAGGGCTTTGTGATCCACGACGGCGAGTGCATGCAGGAGTGCCCCTCGGGC

PheIleArgAsnGlySerGlnSerMetTyrCysIleProCysGluGlyProCysProLysValCysGluGluGluGlu
TTCATCCGCAACGGCAGCCAGAGCATGTACTGCATCCCCTGCGAAGGTCCTTGCCCGAAGGTCTGTGAGGAAGAA

LysLysThrIleAspSerValThrSerAlaGlnMetLeuGlnGlyCysThrIlePheLysGlyAsnLeu
AAGAAAACAATTGATTCTGTTACTTCTGCTCAGATGCTTCAGGGATGCACCATCTTCAAGGGCAATTTG

LeuIleAsnIleArgArgGlyAsnAsnIleAlaSerGluLeuGluAsnPheMetGlyLeuIleGluValValThr
CTCATTAACATCCGACGGGGGAATAACATTGCTTCAGAGCTGGAGAACTTCATGGGCTCATCGAGGTGGTGACG

GlyTyrValLysIleArgHisSerHisAlaLeuValSerLeuSerPheLeuLysSerPheLeuLysAsnLeuGlnGlyIleGlyGly
GGCTACGTGAAGATCCGCCATTCCATGCCCTGGTCTCCTTGTCCCTTAAAAAACCTTCGCCTCATCCTAGGA

GluGluGlnLeuGlyGluGlyLysTyrSerPheTyrValLeuAspAsnGlnAsnLeuGlnLeuTrpAspTrpAsp
GAGGAGCAGCTAGAAGGGAATTACTCCTTCTACGTCCTGGACAACCAGAACTTGCAACTGTGGGACTGGGAC

FIG. 7B

```
                410                                 420                                 430
HisArgAsnLeuThrIleLysAlaGlyLysMetTyrPheAlaAsnProLysLeuLys ValSerGluIleTyr
CACCGCAACCTGACCATCAAAGCAGGGAAAATGTACTTTGCTTTCAATCCAAATTATGTGTTCCGAAATTTAC

ArgMetGluValThrGlyThrLysGlyArgGlnSerLysGlyAspIleAsnThrArgAsnGlyGluArg           1500
CGCATGGAGGAAGTGACGGGGACTAAAGGGCGCCAAAGCAAGGGGACATAAACACCAGGAACAACGGGGAGAGA
                440                                 450                                 480
                                         470
AlaSerCys GluSerAspValLeuHisPheThrThrSerThrSerLeuSerArgIleIleIleThrTrpHis
GCCTCCTGTGAAAGTGACGTCCTGCATTTCACCTCCACCACCGTCGAAGAATCGCATCATCATAACCTGGCAC
                460
ArgTyrArgProAspTyrArgAspLeuIleSerPheThrValTyrTyrLysGluAlaProPheLysAsnVal
CGGTACCGGCCCGACTACAGGGATCTCATCAGCTTTACTACAAGGAAGCACCCTTTAAGAATGTC          1650
                490                                 500
                                              530
ThrGluTyrAspGlyGlnAspAlaCys GlySerAsnSerTrpAsnMetValAspLeuProProAsnLys
ACAGAGTATGATGGCCAGGATGCCTGTGGCTCCAACAGCTGGAACATGGTGGACTTGCCGCCCAACAAG
                510                                 520

AspValGluProGlyIleLeuLeuHisGlyLeuLysProTrpTrpGlnTyrAlaValTyrValLysAlaThr
GACGTTGAGCCCGGCATCTTACTTCACGGCCTGAAGCCGTGGTGGCAAGAGTGTCAAGGCTGTGACC     1800
                                              580
LeuThrMetValGluAsnAspHisIleArgGlyLeuAlaLysSerGluIleLeuTyrIleArgThrAsnAlaSerVal
CTCACCATGGTGGAGAACGACCATATCCGTGGGCTGGCCAAGAGTGAGATCTTGTACATTCGCACCAATGCTTCAGTT
                560                                 570                                 600

ProSerIleProLeuAspValLeuSerAlaSerAsnSerSerGlnLeuIleLeuValLysTrpAsnProProSer
CCTTCCATTCCTTGGACGTTCTTTCAGCATGAACTCCTCTCAGTTAATCGTGAAGTGGAACCCCTCT        1950
                                              630
LeuProAsnGlyAsnLeuSerTyrTyrIleValArgTrpGlnProGlnAspGlyTyrLeuTyrArgHis
CTGCCCAACGGCAACCTGAGTTACTACATTGTCGCTGGAGCCTCAGGACGGGTACCTTTACCGGGCAC
                610                                 620
```

```
                                            880
860                                   870
ArgLysTyrGlyGlyAlaLysLeuAsnArgProGlyAsnTyrThrAlaArgIleGlnAlaThrSerLeu
AGGAAGTATGGAGGGGCCAAGCTAAACCGGGAACTACACAGCCCGGATTCAGGCCACATCTCTC  2850

890
SerGlyAsnGlySerTrpThrAspProValPhePheTyrValGlnAlaLysThrGlyTyrGluAsnPheIleHis
TCTGGGAATGGGTCGTGGACAGATCCTGTGTTCTTCTATGTCCAGGCCAAAACAGGATATGAAAACTTCATCCAT 920                      930
910                  LeuIleIleAlaLeuProValAlaLeuLeuLeuIleValGlyGlyAspGlyValLeuValIleMetLeuTyrValPheHisArg
CTGATCATCGCTCTGCCGGTCGCTGTCCTGTTGATCGTGGGAGGGTTGGTGTTATGCTGTACGTCTTCCATAGA 940                                        950
LysArgAsnAsnSerArgLeuGlyAsnGlyValLeuTyrAlaSerValAlaAsnProGluTyrPheSerAlaAlaAsp
AAGAGAAATAACAGCAGGCTGGGGAATGGAGTGCTGTATGCCTCTGTGAACCCGGAGTACTTCAGCGCTGCTGAT  3000

970                             980
ValTyrValProAspGluTrpGluValAlaAlaArgGluLysIleThrMetSerArgGluLeuGlyGlnSerPhe
GTGTACGTTCCTGATGAGTGGGAGGTGGCTGCTCGGGAGAAGATCACCATGAGCCGGGAACTTGGGCAGGGTCGTTT
                                                           *

1000
990                         GlyMetValTyrGluGlyValAlaAlaLysGlyValValLysAspGluProThrArgValAlaIleLeuLysThrVal
GGGATGGTCTATGAAGGAGTTGCCAAGGGTGTGGTGAAAGATGAACCTGAAACCAGAGTGGCCATTAAAACAGTG  3150

1030
1010                                     1020      AsnGluAlaAlaSerMetArgGluArgIleGluPheLeuAsnGluAlaSerValMetLysGluPheAsnCysHis
AACGAGGCCGCAAGCATGCGTGAGAGGATTGAGTTTCTCAACGAAGCTTCTGTGATGAAGGAGTTCAATTGTCAC 1050
1040                              HisValArgLeuLeuGlyValSerGlnGlyValProThrLeuValIleMetGluLeuMetThrArgGly
CATGTGCGATTGCTGGGTGTGTCCCAAGGGTGTCCCAACACTGGTCATCATGGAACTGATGACACGGGGC  3300

1080
1060                        1070      AspLeuLysSerTyrLeuArgSerLeuValSerLeuArgProGluMetGluAsnProValLeuAlaProProSerLeuSer
CATCTCAAAAGTTATCTCCGGTCTCTGGAGTCCTAGCCAGTCCAGTAATCCAGTCCAGCACCTCCAAGCCTGAGC
```

```
                                                    1100
        LysMetIleGlnMetAlaGlyMetAlaTyrLeuAsnAlaAsnLysPheValHisArgAsp
        AAGATGATTCAGATGGCCGGGATGGCATACCTCAACGCCAATAAGTTCGTCCACAGAGAC     3450
          1090
                                                              1130
        LeuAlaAlaArgAsnCysMetValAlaGluAspPheThrValLysIleGlyAspPheGlyMetThrArgAspIle
        CTTGCTGCCCGGAATTGCATGGTAGCCGAAGATTTCACAGTCAAAATCGGAGATTTTGGTATGACGCGAGATATC
          1110                                 1150
        TyrGluThrAspTyrTyrArgLysGlyLysGlyLeuLeuProValArgTrpMetSerProGluSerLeuLys
        TATGAGACAGACTATTACCGGAAAGGAAAGGGCTGCCCGTGCGCTGGATGTCTCCTGAGTCCCTCAAG        3600
             1140                                1180
        AspGlyValPheThrThrTyrSerAspValTrpSerPheGlyValValLeuTrpGluIleAlaThrLeuAlaGlu
        GATGGAGTCTTCACCACTTACTCGGACGTCTGGTCTTTCGGGGTCGTCCTCTGGGAGATCGCCACACTGGCCGAG
            1160                                 1200
        GlnProTyrGlnGlyLeuSerAsnGluGlnIleValLeuArgPheValMetGluGlyGlyLeuLeuAspLysProAsp
        CAGCCCTACCAGGGCCTTGTCCAACGAGCAAGTCCTTCGTCATGGAGGGCGGCCTTCTGGACAAGCCAGAC       3750
                1190                                 1230
        AsnCysProAspMetLeuPheGluLeuMetArgMetCysTrpGlnTyrAsnProLysMetArgProSerPheLeu
        AACTGTCCTGACATGCTGTTTGAACTGATGCGCATGTGCTGGCAGTATAACCCCAAGATGAGGCCTTCCTTCCTG
             1210                                 1250
        GluIleIleSerSerIleLysGluGluMetGluProGlyPheArgGluValSerPheTyrTyrSerGluAsn
        GAGATCATCAGCAGCATCAAAGAGGAGATGGAGCCTGGCTTCCGGGAGGTCTCCTTCTACTACAGCGAGAACAATAC  3900
                                1240                        1280
        LysLeuProGluProGluGluLeuAspLeuGluProGluAsnMetGluSerValProLeuAspProSerAlaSer
        AAGCTGCCCGAGCCGGAGGAGCTGGACCTGGAGCCAGAGAACATGGAGAGCGTCCCCCTGGACCCCTCGGCCTCC
              1260                                1290
        SerSerSerLeuProAspArgHisSerGlyHisLysAlaGluProGlyValProGlyValVal
        TCGTCCTCCCTGCCCGACAGACACTCAGGACACAAGGCCGAGAACGGCCCCGGGCCCTGGGGTGCTGGTC       4050
                                1300
```

FIG. 7F

```
                1310                    1320                         1330
LeuArgAlaSerPheAspGluArgGlnProTyrAlaHisMetAsnGlyGlyArgLysAsnGluArgAlaLeuPro
CTCCGGGCGAGCTTCGACGAGAGAGACAGCCTTACGCCCACATGAACGGCGGCCGCAAGAACGAGCGGGCCTTGCCG   4200

LeuProGlnSerSerThrCysEnd
CTGCCCCAGTCTTCGACCTGCTGAATCCTGTGCAAACAGTAACGTGTGCGCACGGGCAGCGG                  4350
GGTGGGGGGGAGAGAGTTTAACAATCCATTCACAAGCCTCTGTACCTCAGTGGATCTTCAGTTCTGCCCT          4350
TGCTGCCCGCGGGAGACAGCTTCCTCTGCAGTAAAAACACATTTGGGATGTTCCTTTTTCAATATGCAAGCAGCTT    4350
TTTATTCCCTGCCCAAACCCTTAACTGACATGGGCCTTTAAGAACCCTTAATGACAACACTTAATAGCAACAGAGC    4500
ACTTGAGAACCAGTCTCCTCACTCTGTCCCTGTCCCTTTCTCCCTTTCTCCTGCTTCATAAC                  4500
GGAAAAATAATTGCCACACAAGTCCAGCTGGGAAGCCCTTTTTATCAGTTTGAGGAAGTGGCTGTCCCTGTGCCCC    4650
ATCCAACCACTGTACACCCGCCTGACACGTGGGTCATTACAAAAAACACGTGTTCATCCAAGGCTGTTACCATGGC    4650
TTATCTTTCACCTTTTCTAGGGACATGAACTTTCTCCCTGAACTTTCCTCATTTGCCAATTTTAACGC            4800
TGCCTAATTTGCCAAATCCTGAACTTTCCTCATTTGAGAGACACAGGTCATGGCTCCGTGTCCGGAGGCATGGG      4800
TGAGCATGGCAGCTGGTTGCTGCTCCATTTGAGAGACACAGGTCTCATTGCTTCTGACTAGATTATATTGCCCTGT    4950
GCTGCTCAAGGCCACAGGCACACAGGTCTCATTGCTTCTGACTAGATTATTATTGGGGGAACTGGACACAATAG      4950

GTCTTTCTCAGTGAAGGTGGGGAGAAGCTGAACCGGC                                          4989
```

FIG. 7G

METHOD OF INHIBITING THE PROLIFERATION AND CAUSING THE DIFFERENTIATION OF CELLS WITH IGF-1 RECEPTOR ANTISENSE OLIGONUCLEOTIDES

REFERENCE TO RELATED APPLICATIONS

This application is a continuation of U.S. application No. 08/880,313 filed Jun. 20, 1997 which is a continuation of U.S. application No. 08/479,173, filed Jun. 6, 1995 (issued as U.S. Pat. No. 5,643,788), which is a continuation of U.S. application No. 08/158,176, filed Nov. 23, 1993 (issued as U.S. Pat. No. 5,456,612) which is a continuation-in-part of U.S. application No. 08/037,257, filed Mar. 26, 1993 (now abandoned).

INTRODUCTION

This invention was funded by National Institute of Health Grants GM 33694 and CA 56309. The U.S. government may have certain rights in the invention.

BACKGROUND OF THE INVENTION

The IGF-1 receptor is expressed in many cell types including fibroblasts, epithelial cells, smooth muscle cells, chondrocytes, osteoblasts and several lineages of hemopoietic cells which have IGF-1 receptors and an absolute requirement for IGF-1 for growth in cultures. A review of human cells expressing the IGF-1 receptor and requiring IGF-1 for growth can be found in Baserga and Rubin, *Critical Reviews in Eukaryote Gene Expression*, 1993, 3: 47–61; and Goldring and Goldring, *Eukaryote Gene Expression* 1991, 1, 301–326. Macaulay, *Br. J. Cancer* 1992, 65,311–320, has reviewed the expression of insulin-like growth factors (both IGF-1 and IGF-2) and their receptors in human cancer. Recently, it was shown that IGF-1 peptide analogs may be useful for inhibiting the growth of IGF-1 dependent cells (Pietrzkowski et al., *Cancer Res.* 1993, 53, 1102–1106). Antisense oligonucleotides to mRNA coding for IGF-1 was used to transform rat glioblastoma cells. The cells reversed the transformed phenotype, and acted immunogenic against the parent glioblastoma cell line, completely inhibiting its growth. Trojan et al. *Science,* 1993, 259, 94–97 and Trojan et al., *Proc. Natl. Acad. Sci. U.S.A.,* 1992, 89, 4874–4878. However, effective methods of inhibiting growth and causing differentiation of cells are still greatly desired.

SUMMARY OF THE INVENTION

Methods of inhibiting the growth and causing differentiation of undifferentiated cells with antisense oligonucleotides complementary to a region of the IGF-1 receptor are provided. The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include DNA sequences; and antisense RNA oligonucleotides produced from an expression vector. Each of the antisense oligonucleotides of the present invention are complementary to regions of the IGF-1 receptor sequence. The antisense oligodeoxynucleotide of the present invention comprises a sequence complementary to codons –29 to –24 of the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribodeoxyoligonucleotide, SEQ ID NO: 8 produced from an expression vector comprises a sequence complementary to codons 1 to 309 of the IGF-1 receptor, FIGS. 7A–7G. See Ullrich et al., *EMBO J.,* 1986, 5:2503. Contemplated by this definition are fragments of oligos within the coding sequence for the IGF-1 receptor.

BRIEF DESCRIPTION OF THE FIGURES

FIG. 5A is a schematic representation of cell growth of K10 and C2 cells in 10% serum after 5 days. FIG. 5B is a schematic representation of K10 and C2 cells transfected with T antigen (K10a58 and C2a58 respectively). The K10 cells have not been fully transformed.

FIGS. 7A–7G provide the amino acid and nucleotide sequence of IGF-1 receptor (SEQ ID NO:9).

DETAILED DESCRIPTION OF THE INVENTION

Figure 1A:
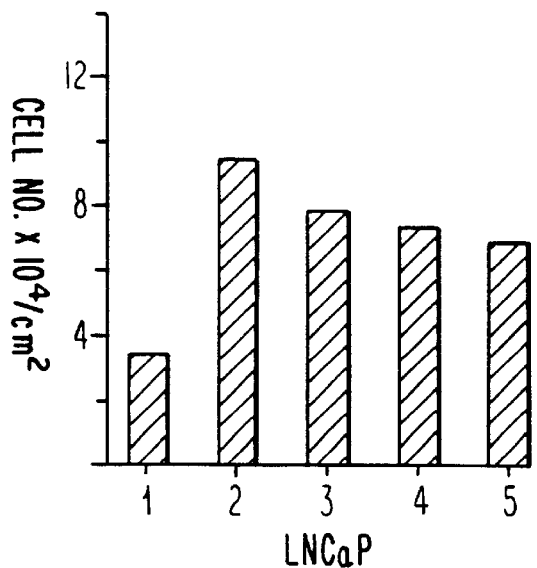
FIGS. 1A–1C are a schematic representation of the effect of individual growth factors on the growth of prostatic cancer cell lines (abscissa). Bars: 1—48 hours after plating; 2—no additions (96 hours after plating); 3—epidermal growth factor (EGF) (20 ng/ml, 96 hours after plating); 4—insulin-like growth factor (IGF-1) (20 ng/ml, 96 hours after plating); 5—platelet derived growth factor (PDGF) (1 ng/ml, 96 hours after plating).

Methods of inhibiting the proliferation of and causing the differentiation of undifferentiated cells are provided by the present invention. In one embodiment, an antisense oligonucleotide having a sequence complementary to codons –29 to –24 of the signal sequence of the IGF-1 receptor was found to be effective.

For purposes of the present invention, undifferentiated cells include and are not limited to transformed cells, cancer cells, prostate cancer cells, ovarian cancer cells, mammary cancer cells, lung cancer cells, glioblastoma cells, smooth muscle cells, bone marrow stem cells, hematopoietic cells, osteoblasts, epithelial cells, fibroblasts. Abnormal cells are cells which do not grow in accordance with the predicted patterns of a selected cell type, including and not limited to cancer cells such as those identified above, and transformed cells.

For purposes of the current invention, mammals include, but are not limited to the Order Rodentia, such as mice;

Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include single stranded DNA sequence and an antisense RNA oligonucleotide produced from an expression vector. Each of the antisense oligonucleotides of the present invention are complementary to regions of the IGF-1 receptor sequence. The antisense oligodeoxynucleotide of the present invention comprises a sequence complementary to codons −29 to −24 of the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribonucleotide, SEQ ID NO: 8 produced from an expression vector comprises a sequence complementary to codons 1 to 309 of the IGF-1 receptor, FIGS. 7A–7G. See Ullrich et al., *EMBO J.*, 1986, 5:2503. Contemplated by this definition are fragments of oligos within the coding sequence for the IGF-1 receptor. In addition, mismatches within the sequences identified above, which achieve the methods of the invention, such that the mismatched sequences are substantially complementary to the IGF-1 sequences identified above, are also considered within the scope of the disclosure. Mismatches which permit substantial complementarity to the IGF-1 sequences will be known to those of skill in the art once armed with the present disclosure. The oligos may also be unmodified or modified.

The present invention is also directed to a method of treating mammals having cancer comprising contacting the mammal with an effective amount of an antisense oligonucleotide having a sequence which is complementary to a region of the IGF-1 receptor RNA. Cancer cells contemplated by the present invention include and not limited to those identified above.

Methods of administering the antisense oligos of the present invention include techniques well known in the art such as and not limited to liposomes, plasmid expression, retroviral vectors, splicing an oligo to another sequence such as a promoter or a growth factor, wherein the plasmid and/or vector is transfected with an expression plasmid expressing the antisense oligonucleotide, exposing cells to a medium or wash containing the oligo. In the administration of oligos via vectors or plasmids, a non-coding RNA strand of IGF-1 receptor is preferably used in order to produce antisense RNA oligos which are expressed by the cell. The RNA oligos then bind IGF-1 sense or coding RNA sequence. Accordingly, an oligo RNA sequence similar to SEQ ID NO: 4 is used. In the administration of a medium or wash, antisense DNA is preferably an oligo DNA, similar to SEQ ID NO: 4, and SEQ ID NO: 7.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting IGF-1 receptors at the same time. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton, Pa. The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty $\mu$g/ml antisense oligo was used for in vitro methods of providing oligos in media for cell growth in culture. This concentration may be extrapolated for in vivo use. The concentration of antisense oligodeoxynucleotides for in vivo use is about 40 $\mu$/g body weight. The in vivo use of the expression vector expressing RNA oligonucleotides is determined by the number of transfected cells.

The growth of prostatic cancer cell lines was inhibited by antisense oligonucleotides to IGF-1 receptor RNA indicating that these cells need a functionally activated IGF-1 receptor for growth. These compositions are nontoxic at the concentrations used and are very effective and easy to deliver. These compositions may be useful in the treatment of prostatic cancer and other forms of abnormal growth because IGF-1 is a required growth factor for a wide variety of cell types and its action seems to be located downstream from other growth factors receptors. Therefore, while cells could circumvent other growth factor requirements by establishing an IGF-1/IGF-1 receptor autocrine loop, for many cell types, the activation of the IGF-1 receptor is the last receptor-mediated event before DNA synthesis and mitosis, and, presumably cannot be circumvented except by intracellular substrates of the IGF-1 receptor. Methods of reversing the transformed phenotype of cells with abnormal growth potential are also provided.

Figure 1B:
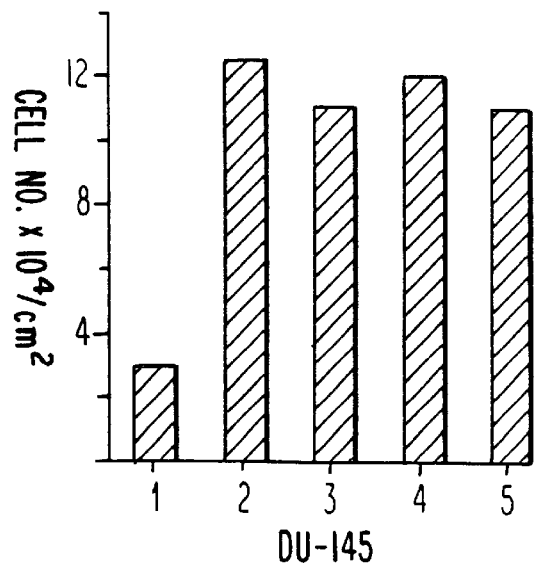
Figure 1C:
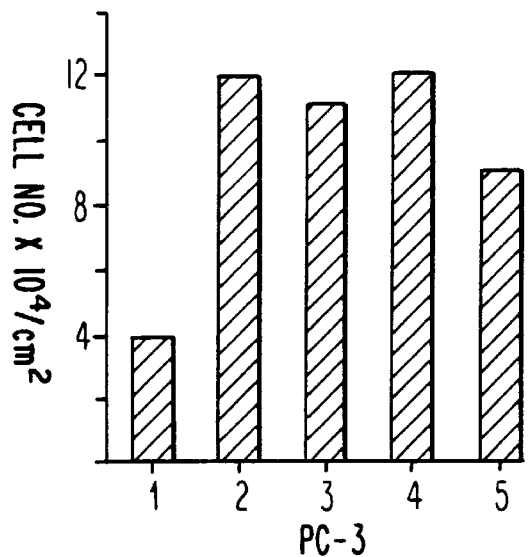
Figure 2:
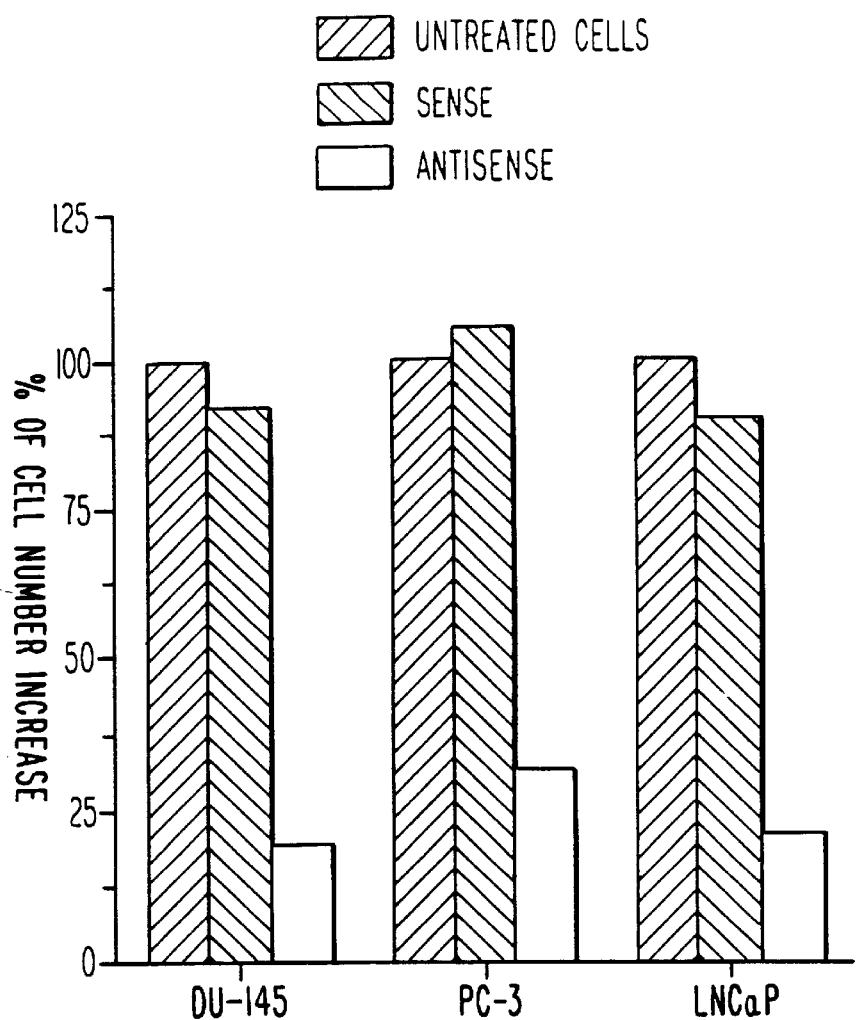
FIG. 2 is a schematic representation of the effect of antisense oligonucleotide to the IGF-1 receptor on the growth of prostatic cancer cell lines. Bars 1, 4, and 7 (control). Bars 2, 5, and 8 (sense). Bars 3, 6, and 9 (antisense).

In one series of experiments, well established cell lines that were adapted to grow in vitro and that originated from sources of human prostatic cancer are examined. The effect of individual growth factors on the growth of these prostatic cancer cell lines is shown in FIGS. 1A–1C. The effect of an antisense oligodeoxynucleotide to the IGF-1 receptor RNA on the growth of these cells lines is shown in FIG. 2. The effects of antisense oligodeoxynucleotide to the IGF-1 receptor RNA on the growth of Balb 58 cells, human glioblastoma cells, human ovarian cancer cells, and HL-60 cells are also shown. As the data show, these cells need a functionally activated IGF-1 receptor for growth. Any cells having an IGF-1 receptor may be targeted by methods of the present invention. For example, leukemic cells, cancer cells, and smooth muscle cells may be targeted by methods of the present invention. The potential usefulness of such an antisense composition in the treatment of prostatic cancer and other forms of abnormal growth is shown by the observation that IGF-1 is a required growth factor. In other words, while the cells could circumvent other growth factor requirements by establishing an IGF-1/IGF-1 R autocrine loop, the activation of the IGF-1 receptor (IGF-1R) is the last receptor-mediated event before DNA synthesis and mitosis, and presumably, cannot be circumvented except by intracellular substrates of the IGF-1 receptor. The experiments show that the IGF-1/IGF-1 receptor pathway plays an important role in the growth and differentiation of cancer cell lines and that antisense composition can inhibit their growth and cause differentiation.

Furthermore, methods of reversing transformed phenotype of cells with abnormal growth potential are provided by the present invention. For example, since the absence of IGF-1 receptor has been found to decrease cell growth by 70%, but completely inhibits the transformed phenotype, this approach can differentially affect cells having an abnormal phenotype, such as cancer cells, by reversing the transformed phenotype at concentrations of antisense that only partially affect normal growth. Reversal of the transformed phenotype causes differentiation that is usually irreversible. Furthermore, the cells may become immunogenic towards themselves providing an additional benefit.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

The invention is further illustrated by the following, non-limiting examples.

EXAMPLES

Experiment A

Example 1

Cell Lines

The following cells lines were used.
1) Balb/c 3T3 cells;
2) mouse embryo cells established as primary cultures from normal mouse embryo;
3) KO cells, established from littermate embryos, null for the IGF-1 receptor;
4) three human prostatic cancer cell lines obtained from the American Tissue Culture Collection: PC-3 (originating from a human adenocarcinoma of the prostate; ATCC# HTB81); LNCa.FGC ("LNC"; from a human metastatic adenocarcinoma of the prostate, ATCC# CRL1740); and DU-145 (from a human carcinoma of the prostate metastatic to the brain, ATCC# CRL1435);
5) a human ovarian carcinoma cell line, ON-CAR; ATCC# HTB161
6) Balb 58 cells, Porcu et al., *Mol. Cell. Biol.* 1992, 12, 5069–5077;
7) T98G cells, a glioblastoma cell line originating from a human glioblastoma; and
8) HL-60 cells, a well established human promyelocytic cell line.

Human prostatic cell lines were passaged as recommended by the ATCC; they are grown in the following serum free media: DU-145 in MEM supplemented with 1 $\mu$M ferrous sulfate, 1 mM sodium pyruvate and 0.1% bovine serum albumin (BSA). The same supplements were added to DMEM:RPMI 1640 (1:1) to grow PC-3 cells, and to RPMI 1640 for LNC cells.

Example 2

Growth in Serum-free Medium

The cells were plated first in 10% calf serum in order to provide attachment factor. Alternatively, poly-L-lysine may be used. Pietrzkowski et al., *Mol. Cell. Biol.* 1992, 12, 3883–3889. The growth medium was removed by careful and repeated washing after twenty four hours and replaced with serum-free medium, with the sole additions of bovine serum albumin (0.5 mg/ml) and ferrous sulfate, 1.0 $\mu$M. The number of cells was determined by standard methods at the times indicated in each individual experiment. All three cell lines, DU-145, PC-3, and LNC grow in serum-free medium as vigorously as in serum supplemented medium, unlike 3T3, p6 and human diploid fibroblasts which do not grow under serum-free conditions. Pietrzkowski et al., *Mol. Cell. Biol.* 1992, 12, 3883–3889.

Example 3

Effect of Growth Factors on Prostatic Cancer Cell Lines

Cells were cultured as described in Example 2. Epidermal growth factor (EGF) (20 ng/ml), platelet derived growth factor (PDGF) (1 ng/ml) or insulin-like growth factor-1 (IGF-1) (20 ng/ml) were added to individual cell cultures. No increase in cell growth was observed 96 hours after plating of DU-145 and PC-3 cell lines. The growth factors showed slight inhibitory effects on LNC cells 96 hours after plating.

Example 4

Reverse-Transcriptase Polymerase Chain Reaction (RT-PCR)

The prostatic cancer cell lines were tested for their ability to express IGF-1 receptor RNA by RT-PCR after incubation of cells in serum-free medium for 48 hours. Reverse-transcriptase polymerase chain reaction was performed by slight modification of the method of Rappolee et al., *J. Cell.*

Biochem. 1989, 39, 1–11; Lipson et al., *Proc. Natl. Acad. Sci. U.S.A.* 1989, 86, 9774–9777. RNA was extracted from cells by slight modification of the method of Chomczynski and Sacchi, *Anal. Biochem.* 1987, 162, 156–159. Amplimers and probe for the IGF-1 receptor RNA were chosen on the basis of the published cDNA sequence of the human IGF-1 receptor. Ullrich et al., *EMBO J.* 1986, 5, 2503–2512. 5' amplimer, 5' ACC ATT GAT TCT GTT ACT TC 3' (SEQ ID NO: 1); 3' amplimer, 5' ATA CTC TGT GAC ATT CTT AA 3' (SEQ ID NO: 2); probe, 5' CTG CTC CTC TCC TAG GAT GA 3' (SEQ ID NO: 3). Labeling of probes and hybridization were carried out by standard methods as described for example by Feinberg and Vogelstein, *Anal. Biochem.* 1983, 132, 6–13 and Thomas, P. S., *Methods Enzymol.* 1983, 100, 255–266. The various controls used in the RT-PCR assays (elimination of DNA, rejection of samples that give signals without reverse transcriptase, and multiple amplification cycles) are described for example by Pietrzkowski et al., *Cell Growth & Diff.* 1992, 3, 199–205; Pietrzkowski et al., *Mol. Cell. Biol.* 1992, 12 3883–3889; Reiss et al., *Oncogene* 1992, 7, 2243–2248. RNA amounts were monitored with amplimers and probe for the pHE 7 cDNA, ribosomal protein cDNA, whose cognate RNA is expressed constantly under different conditions of growth. Reiss et al., *Oncogene* 1992, 7, 2243–2248.

Figure 3:
FIG. 3 is an autoradiogram of RT-PCR to determine the level of IGF-1 RNA produced by 5 different cell lines. Lane 1: PC-3; Lane 2: DU-145; Lane 3: LNC cells; Lane 4: WI-38 human diploid fibroblasts; Lane 5: p12 cells.

Results are shown in FIG. 3. RNAs from PC-3 cells (lane 1), DU-145 cells (lane 2), LNC cells (lane 3), WI-38 human diploid fibroblasts (lane 4, normal control) and p12 cells (which constitutively overexpress IGF-1 receptor RNA; lane 5) are shown. WI-38 cells and p12 cells were included as examples of cells which require IGF-1 for growth. Chomczynski, and Sacchi, *Anal. Biochem.* 1987, 162, 156–159.

Two of the cell lines, PC-3 and DU-145 express levels of IGF-1 receptor RNA that are about 10-fold (by densitometry) the levels in WI-38 cells. LNC cells express levels that are only slightly above those of WI-38. The amounts of RNA in each reaction were within 10% of each other.

Example 5

Antisense Experiments

Antisense and sense oligonucleotides corresponding to portions of codon −29 to −24 of the signal sequence of the human IGF-1 receptor preceding the proreceptor sequence, Ullrich et al., *EMBO J.* 1986, 5, 2503–2512 were prepared. The oligodeoxynucleotides were synthesized on an Applied Biosystem Model 391 EP DNA synthesizer using β-cyanoethyl phosphoramidite chemistry. Pietrzkowski et al., *Cell Growth & Diff.* 1992, 3, 199–205; Pietrzkowski et al., *Mol. Cell. Biol.* 1992, 12, 3883–3889; Reiss et al., *Oncogene* 1992, 7, 2243–2248.

Phosphorothioate oligonucleotides having sequences corresponding to codons −29 to −24 of the signal sequence, having the sequences TCCTCCGGAGCCAGACTT (SEQ ID NO: 4; antisense) and GCACCGGGAAGTTGTGTCAA (SEQ ID NO: 6; mismatched) were prepared as described above. 40 μg/ml of the oligonucleotides were added to SV-40 transformed Balb 58 cells (L clone; Porcu et al., *Mol. Cell. Biol.* 1992, 5069–5077), in 1% serum at 34° C. The cells were counted after 72 hours. The antisense oligonucleotide caused an 85% inhibition of cell growth as compared to a control (no addition of oligonucleotide). The mismatched antisense oligonucleotide resulted in only a 15% inhibition of cell growth.

Three human prostatic cancer cell lines were also treated with antisense phosphorothioate oligonucleotides. The oligonucleotides had the sequences TCCTCCGGAGCCAGACTT (SEQ ID NO: 4; antisense) and AAGTCTGGCTCCGGAGGA (SEQ ID NO: 5; sense). Pietrzkowski et al., *Cell Growth & Diff.* 1992, 3, 199–205. The oligodeoxynucleotides were added to the medium after 48 hours in serum-free medium (40 μg/ml) and the treatment was repeated the next day (20 μg/ml). The cells were counted 48 hours after the second addition. FIG. 2 shows that antisense oligonucleotides to IGF-1 receptor RNA markedly inhibited all three prostatic cancer cell lines, the inhibition varying from 70 to 90%. After 48 hours treatment, the prostatic cancer cells look flat, polygonal, with the characteristics of a normal epithelial cell.

Antisense studies were also carried out on an ovarian carcinoma cell line and on a glioblastoma cell line. The results are summarized in Table 1.

TABLE 1

Effect of Antisense Oligodeoxynucleotides to the
IGF-1 Receptor RNA on the Growth of Human Cancer Cell Lines

| | Inhibition of growth % | |
|---|---|---|
| cell lines | antisense | sense |
| T98G (human glioblastoma) | 90 | 12 |
| ON-CAR (human ov.ca.) | 100 | 2 |

Cells were grown in serum-free medium supplemented with individual growth factors and the antisense or sense phosphorothioate oligonucleotides at concentrations of 40 μg/ml. The oligonucleotides had the sequences TCCTCCGGAGCCAGACTT (SEQ ID NO: 4; antisense) and AAGTCTGGCTCCGGAGGA (SEQ ID NO: 5; sense). The inhibition is based on the growth of control cells (no oligos added). Cells treated with antisense showed signs of differentiation, with flattening, contact inhibition and reversal of the transformed phenotype.

HL-60 cells were also treated with the antisense phosphorothioate oligonucleotides. The oligonucleotides had the sequences TCCTCCGGAGCAGACTT (SEQ ID NO: 4; antisense) and AAGTCTGGCTCCGGAGGA (SEQ ID NO: 5; sense). When HL-60 cells were treated with antisense oligonucleotides to the IGF-1 receptor RNA, the cells differentiated toward a macrophage lineage, just as when they are treated with a differentiating agent.

Example 6

Autophosphorylation of the IGF-1 Receptor

Figure 4:
FIG. 4 is a western blot showing autophosphorylation of IGF-1 receptor. Lane 1: p12 cells 48 hours in serum-free medium, Lanes 2–4: PC-3, DU-145, and LNC cells respectively, 48 hours in serum-free medium 15 minutes after the addition of IGF-1 (3 ng/ml), Lanes 5–7: PC-3, DU-145 and LNC cells respectively, 48 hours in serum-free medium, no added IGF-1.
Figure 7D:
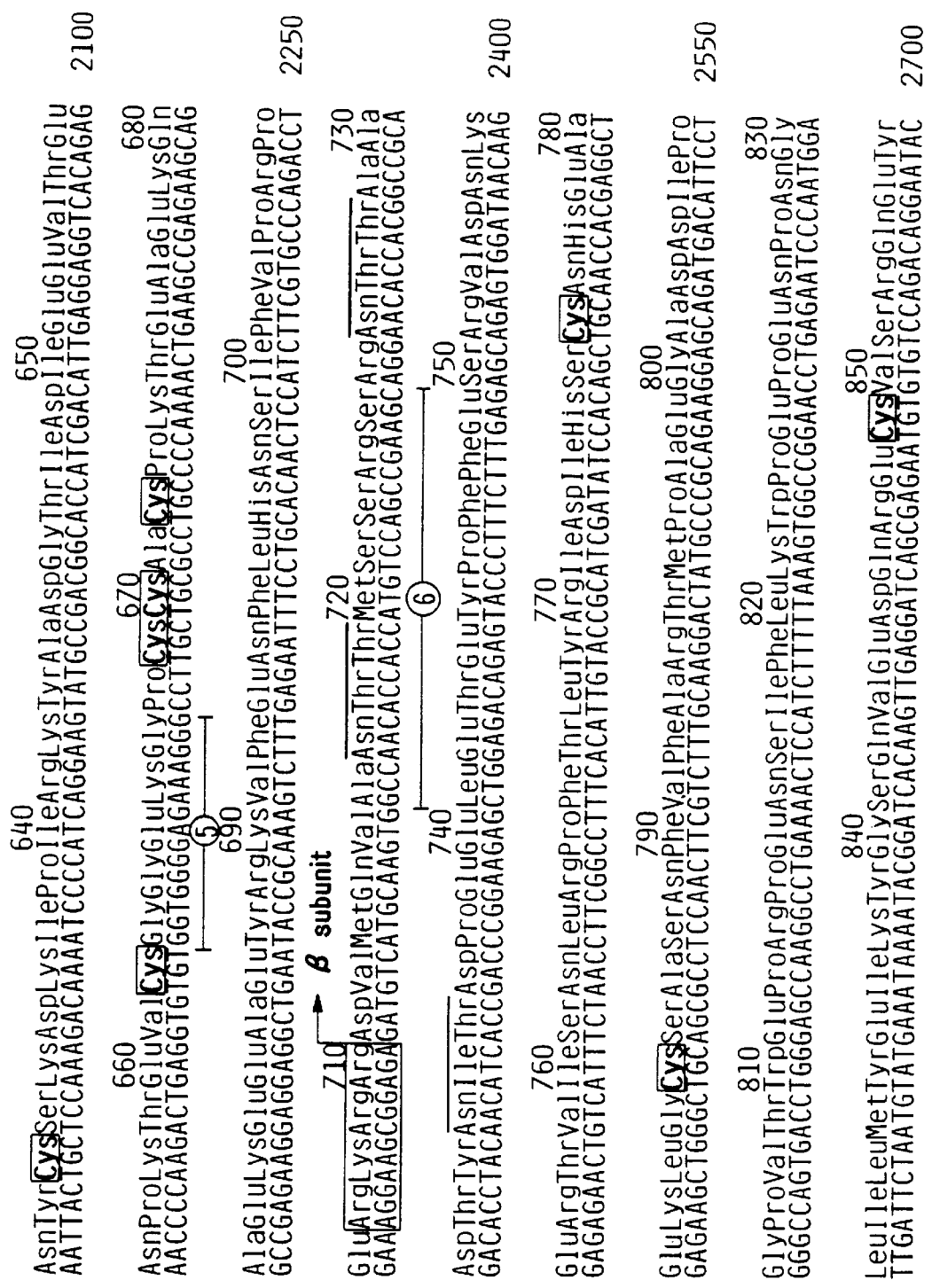

The cells were characterized for levels of IGF-1 receptor that can be autophosphorylated by IGF-1. Autophosphorylation was carried out by slight modification of the method of Lammers et al., *EMBO J.* 1989, 8, 1369–1375, using the monoclonal antibody to the IGF-1 receptor available from Oncogene Sciences (Uniondale, N.Y.), an anti-phosphotyrosine antibody available from UBAI (Saranac Lake, N.Y.), and the ECL detection system kit from Amersham (Arlington Heights, Ill.). Protein lysates were obtained from cells growing for 48 hours in serum free medium. Before lysis, the cells were treated for 2 hours with sodium orthovanadate (1 mM). Results are shown in FIG. 4.

Although the amount of autophosphorylated IGF-1 receptor is not as high as in p12 cells (lane 1), which constitutively overexpress the human IGF-1 receptor, substantial amounts of receptor that can be autophosphorylated by IGF-1 are detectable in all cell lines (lanes 2–4). More significantly, the autophosphorylation of the receptor can be detected in cells growing in serum-free medium even without the addition of IGF-1 (lanes 5–7), indicating that, in these cell lines, the IGF-1 receptor is constitutively autophosphorylated due to the presence of measurable amounts of IGF-1 secreted by the cells themselves into the medium.

Example 7

IGF-1 Radioimmune Assay

The ability for the cells to produce and secrete IGF-1 in the medium was determined by radioimmune assay. The radioimmune assay was performed essentially as described by Pietrzkowski et al., *Mol. Cell. Biol.* 1992, 12, 3883–3889. Cells were incubated in serum-free medium for 72 hours. Conditioned medium containing 1% bovine serum albumin (BSA) and 1 mM ferric sulfite was collected at various times after the cells were transferred to serum-free medium. To remove IGF-1 binding proteins, 0.1 ml of conditioned medium was mixed with 900 ml of 1 M acetic acid and 5% BSA and loaded onto SepPak C18 columns (Waters, Milford, Mass.). Before loading, the column was washed with 10 ml of methanol and then by 10 ml $H_2O$. After loading, the column was washed with 10 ml of 4% acetic acid, and IGF-1 was eluted in 1 ml of 50% acetonitrile and 4% acetic acid. After lyophilization, the sample was resuspended directly in 100 ml of radioimmunoassay buffer. The assay was performed with a rabbit IGF-1 anti-serum and a second antibody bound to magnetic beads (Amersham, Arlington Heights, Ill.) using a commercially available radioimmunoassay kit (Amersham, Arlington Heights, Ill.). The results are shown in Table 2.

TABLE 2

| Cell Line | Amount of IGF-1 in ng IGF-1/ml/2 × $10^6$ cells |
|---|---|
| DU-145 | 12.06 |
| LNC | 14.38 |
| PC-3 | 24.36 |

As seen in TABLE 2, all three cell lines are good producers of IGF-1, especially PC-3. In all instances, however, the concentration of IGF-1 is more than sufficient to autophosphorylate the IGF-1 receptor and to sustain growth if the number of IGF-1 receptors is adequate.

For example, ordinarily, in cells expressing an adequate number of IGF-1 receptors, like p6 cells, 3.0 ng/ml of IGF-1 are sufficient to induce autophosphorylation of the receptor and stimulation of growth.

Example 8

SV40 T antigen

For transformation, pts58H, a plasmid which contains the tsA58 T antigen coding gene, cloned in pBR322, was used as well as the hygromycin resistance hph cDNA under the control of a viral promoter. Porcu et al., *Mol. Cell. Biol.*, 1992, 12, 5069–507. Clones of cells transfected with this construct are selected in hygromycin.

KO cells (no IGF-1 receptors) grow in 10% serum at a rate that is roughly 40% the rate of wild type cells (MEC cells). IAs shown in FIG. 5A, these cells are indicated as K10 and C2 cells. Both MEC and KO cells were transfected with the plasmid tsA58H, carrying the SV40 T antigen and a selectable marker. Clones were selected in hygromycin; because of the plasmid used, all cells in all clones were 100% T antigen positive.

FIG. 5B shows the growth characteristics of these two types of cells, transfected with T antigen, and which we call KI 0a58 and C2a58. The figure gives the saturation density of these two cell lines. The saturation density of C2a58 cells is 4-fold the saturation density of KI 10a58. The latter one formed a contact-inhibited monolayer, while C2a58 cells were forming foci, like transformed cells. This suggests that T antigen has not been able to fully transform the KO cells.

Example 9

Soft agar assay was carried out by standard methods. A more convincing way to test for transformation is to grow cells in soft agar, a test that has been used for many years to characterize transformed cells. Untransformed cells do not form colonies in soft agar; only transformed cells can form colonies, and the number of colonies formed is usually taken as an index of transformation. Cells were tested in soft agar, and the results of such an experiment are shown in TABLE 3.

TABLE 3

Growth in Soft Agar of Various Cell Lines

| cell line | number of colonies formed |
|---|---|
| Balb/c 3T3 cells | 0 |
| Balb58 cells (transformed 3T3) | >200 |
| T98G (human glioblastoma) | >100 |
| MEC cells | 0 |
| KO cells | 0 |
| T-MEC cells (T transformed) | >200 |
| T-KO cells (T-transfected) | 0 |

One thousand cells of each cell line were seeded and the number of colonies determined after 2 weeks.

The prostatic cancer cell lines and the ovarian carcinoma cell line also grow in soft agar, as reported by other investigators. TABLE 3 clearly shown that a strong oncogene like SV40 T antigen is incapable of transforming cells that do not have IGF-1 receptors. Experiments are in progress in nude mice: preliminary data indicate, as anticipated, that T-KO cells do not grow in nude mice, whereas other T-transformed mouse cells do.

EXPERIMENT B

Example 10

Cell Cultures and Plasmid Construction

Mouse embryos were dissected from anesthetized females at day 18 of gestation and genotyped using DNA prepared from the mouse tails by Southern analysis as described by Liu, et al., *Cell,* 1993, 75:59 and Baker et al., *Cell,* 1993, 75:73. Wild-type and homozygous IGF-1 receptor mutant (Igflr (-1-)) littermates were used for establishing primary cultures of embryonic fibroblasts as described by Warton, et al., in *Cell Growth and Division,* 1989, 139–153, Baserga, ed, IRL Press, Oxford, England.

The embryos were minced, and treated with trypsin for 15 minutes. The cells of the resulting suspension were plated onto 100 mm culture dishes and cultures in Dulbecco's modified Eagle's medium (DMEM:GIBCO-BRL, Grand Island, N.Y.) supplemented with 10% fetal bovine serum. The cultures were maintained at subconfluent levels by trypsinizing every three days and reseeding at a density of $1.5 \times 10^3$ cells/$cm^2$, following the same protocol used to generate 3T3 cell lines. Todaro, et al., *J. Cell Biol.*, 1963, 17, 299. Primary cultures underwent crisis following 2–4 weeks in culture. Crisis results in immortalized cells. Cells null for IGF-1 receptor, R-, cultures entered crisis later than the wild-type cells due to the relatively slow doubling rate.

Cells from wild-type and homozygous Igf1r (-1-) mutant embryos were established initially as primary cultures and subsequently as post-crisis cell lines, which will be referred to as parental lines W and R-, respectively. These lines, which were derived by a protocol previously used to generate 3T3 cells, have a fibroblast-like appearance. Todaro, G. J. et al., *J. Cell Biol.*, 1963, 17:299. In serum-free medium supplemented with PDGF (5 ng/ml), EGF (20 ng/ml) and IGF-1 (20 ng/ml), W cells grow well, while R- cells fail to increase in number. Growth of R- cells can be sustained in 10% serum, but their growth rate is only 40–50% that of W cell controls (see TABLE 4). The growth of W cells under the conditions of TABLE 4 is essentially the same as that of the Balb/c 3T3 cells.

TABLE 4

GROWTH OF W AND R- CELLS IN CULTURE

| CELL TYPE | GROWTH FACTORS | NUMBER OF DOUBLINGS |
|---|---|---|
| W Cells | PDGF, EGF, IGF-1 | 1.5 |
| W Cells | 10% serum | 3.0 |
| W Cells | serum-free medium | 0 |
| R- Cells | PDGF, EGF, IGF-1 | 0 |
| R- Cells | 10% serum | 1.5 |
| R- Cells | Serum-free medium | 0 |

Cells were seeded at a concentration of 5 × 10 cells/cm in plastic dishes, in DMEM supplemented with 10% fetal calf serum. After 24 hours, the growth medium was removed, the cells washed several times with Hanks' solution and DMEM was added with the indicated supplements. Cells were counted at 48 and 72 hours after changing to the indicated condition. The number of doublings shown represents 72 hours.

Indirect biochemical analysis showed that a functional IGF-1R is absent from primary cultures of cells isolated from day 14.5 Igf1r (-1-) mutant embryos. Liu, et al., *Cells*, 1993, 75:59 and Baker et al, *Cell*, 1993 75:73. To confirm this result using a specific antibody and establish unequivocally that R- cells are completely devoid of IGF-1 receptor, the following experiment was performed.

After incubation in the presence of IGF-1 for ligand-activated autophosphorylation of the IGF-1 receptor, R- cells and control W cells were lysed and a polyclonal antibody against the β subunit of mouse IGF-1 receptor was added to immunoprecipitate and functional IGF-1 receptor present in the lysate. The precipitated proteins were solubilized in the presence of β-mercaptoethanol, resolved electrophoretically and transferred to a nitrocellulose membrane. The β subunit of IGF-1 receptor autophosphorylated in an IGF-1-dependent fashion, was visualized by immunostaining with an anti-phosphotyrosine antibody (UBL, Saranac Lake, N.Y.) and recognized by size, and by the response to IGF-1. The apparent molecular weights of the α and β subunits of IGF-1 receptor resolved electrophoretically after disulfide bond reduction and denaturation are 135 kD and 97 kD, respectively. Autophosphorylation of β subunit (97 kD species) was detected, after IGF-1 stimulation, in W cells, but not in R- cells.

For confirmation the presence of the α subunit of the IGF-1 receptor was examined by cross-linking radioiodinated IGF-1 to cell membranes, followed by electrophoretic analysis and autoradiography. Yamori, et al., *Cancer Res.*, 1991, 51, 5859. A labeled protein of 135 kD was easily detectable in W cells, and its signal could be eliminated by competing the radioiodinated ligand with a 1,000 fold excess of unlabeled IGF-1. In contrast, it was not possible to detect a labeled protein species of this size in R- cells, even after significant overexposure of the autoradiogram.

Figure 6:
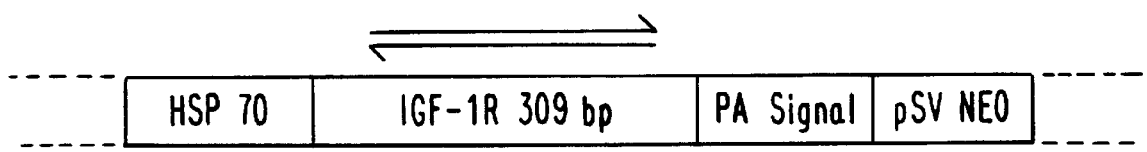
FIG. 6 is a diagram of the plasmid constructs IGF-1RS and IGF-1RAS.

T98G cells are a human glioblastoma cell line, that produces large amounts of IGF-1. Stein, G. H., *J. Cell. Physiol.*, 1979, 99:43. Two other cell lines were generated from T98G cells, expressing, respectively, a sense and an antisense RNA to the human IGF-1 receptor RNA. Expression plasmids which generate mRNA sequences, sense or antisense to the human IFG-1 receptor, were constructed. The human heat shock promoter HSP 70 was excised from the pSp2 (Craig et al., *Cell*, 1979, 16:575) with PstI and inserted into the SalI site of the pUC 18 multiple cloning site (MCS). The hepatitis B polyadenylation (PA) signal sequence and a neomycin resistance gene under control of the simian virus 40 (SV40) promoter were cloned into the BamHI site of the multi-cloning site to generate the plasmid HSP-neo. An XbaI-XhoI fragment corresponding to the bp 1–309 of the IGF-1 receptor cDNA (Ullrich et al., *EMBO J.* 1986, 5, 2503–2512) was filled-in with Klenow, and blunt end ligated into a filled-in BamHI site of the plasmid HSP-neo. The resulting plasmids were restricted and sequenced to determine the orientation of the transcripts. The plasmids predicted to produce the sense and antisense transcripts of the IGF-1 receptor cDNA were named HSP-IGF-1RS and HSP-IGF-1RAS, respectively, see FIG. 6. Transfections were performed using the calcium phosphate precipitation method (Shen et al., *Mol. Cell. Biol.*, 1982, 2:1145). After 48 hours, 1 mg/ml neomycin was added to the cells to obtain stable transfectants.

Cells were seeded at a density of 3×10$^3$/35 mm plate in 10% serum on a top layer of 0.3% agar and a bottom support layer of 1% agar. Colonies of greater than 10 cells were counted 14–21 days later.

C6 cells are a rat glioblastoma cell line. Trojan et al., *PNAS*, 1992, 89:4874 and Trojan et al., *Science*, 1993, 259:94.

Example 11

Plasmid Transfection

Cells were transfected with DNA of the following plasmid constructs: a) ptsA58H (Porcu, et al., *Mol. Cell. Biol.*, 1992, 12:5069) which contains the hygromycin-resistance gene (hyg) and the sequence encoding tsA58, a temperature-sensitive SVLT (Tegtmeyer, *J. Virol.*, 1975, 15:613); b) pSV2G (Floros, et al., *Exp. Cell Res.*, 1981, 132:215), which contains the sequence encoding the wild-type SV40 T antigen and which was co-transfected with a plasmid containing the hygromycin resistance gene (LHL4) (Gritz, et al., *Gene*, 1983, 25:179); and c) Cvn-IGF-1 receptor, which contains the neomycin resistance gene (neo) and the entire coding sequence of the human IFG-1 receptor cDNA, both of which are under control of the SV40 promoter; as described by Porcu, et al., *Mol. Cell. Biol.*, 1992, 12, 5069.

Primary cultures were extremely sensitive to hygromycin and selection was carried out in 10 μg/ml of hygromycin. Cell proliferation in anchorage-dependent conditions was assayed by trypsinizing the cells and counting in triplicate every 24 hours, using a hemocytometer.

Parental W and R- cells were transfected with DNA of a plasmid construct ptsA58H (Porcu, et al., *Mol. Cell. Biol.*, 1992, 12, 5069), containing a selectable marker, the hygromycin-resistance gene (Gritz et al., *Gene*, 1983 25:179), and the sequence encoding the temperature-sensitive SV40T antigen tsA58 (Tegtmeyer, *J. Virol.*, 1975, 15:613). Cells expressing tsA58 are transformed at the permissive temperature of 34 C, but revert to the untransformed phenotype at the restrictive temperature of 39.6 C (Porcu et al., supra, Lammers, et al., *EMBO J*, 1989, 8:1369, Jat, et al., *Mol. Cell. Biol.,* 1989, 9:1672, Radna et al., *Molc. Cell. Biol.,* 1989, 9:3093, and Resnick-Silverman et al., *J. Virol.,* 1991, 65:2845). Since the selectable marker and T antigen are expressed from the same plasmid, all of the hygromycin-resistant clones derived were also T-positive. Thus, when selected W and R- cells harboring ptsA58H were examined by immunofluorescence using an antibody against T antigen, both cell types exhibited approximately the same level of intensity in staining (45±0.9 and 43.7±0.7 arbitrary densitometric units respectively). These transfected derivatives of the parental W and R- lines were designated (tsA)W and (tsA)R-cells.

The four types of cells [W, R-, (tsA)W and (tsA)R-] were plated and grown in DMEM supplemented with 10% serum for 5 days, and then cell numbers were determined to assess saturation densities. As expected from previous results, the ratio of R- to W cell numbers was 0.53. However, growth was differentially stimulated by the presence of SVLT. The number of (tsA)W cells was 2.7 fold higher than that of W cells, while (tsA)R- cells grew only 30% above the saturation density of the R- parent. More importantly, the (tsA)W cells were overtly transformed, as evidenced by the appearance of large foci, while the (tsA)R- cells continued to be contact-inhibited. Identical results were obtained with several different T positive clones derived from the parental cell lines.

To further assess the presence or absence of a transformed phenotype, we used soft-agar assays (Thompson, et al., *Virology,* 1990, 178:15). The results of a typical experiment are shown in TABLE 5. As expected, (tsA)W cells formed colonies in soft agar in numbers increasing with the number of cells that were seeded, while only a single small colony of 12 cells appeared with the highest number of plated (tsA)R- cells. The cells were maintained in 10% serum for more than 3 weeks, which is a more than adequate time period for establishment of colonies in soft agar even at reduced growth rates. Therefore, the (tsA)R- cells do not have potential for colony formation in soft agar.

TABLE 5

GROWTH IN SOFT AGAR OF MOUSE
EMBRYO CELLS EXPRESSING SVLT

| CELL TYPE | SEEDING DENSITY × $10^3$ | NUMBER OF COLONIES |
| --- | --- | --- |
| (tsA)W | 1 | 8 |
| (tsA)W | 10 | 64 |
| (tsA)W | 100 | 350 |
| (tsA)R- | 1 | 0 |
| (tsA)R- | 10 | 0 |
| (tsA)R- | 100 | 1 |
| (wtT)W | 10 | 58 |
| (wtT)W | 100 | 154 |
| (wtT)R- | 10 | 0 |
| (wtT)R- | 100 | 0 |
| (tsA)R+ | 10 | 16 |
| (tsA)R+ | 100 | 70 |

(tsA)W and (tsA)R- are, respectively, W and R- cells expressing the tsA58 T antigen. The same embryo cells expressing the wt T antigen are designated (wtT). (tsA)R+ cells are (tsA)R- cells expressing a stably transfected human IGF-1 receptor cDNA. Parental cell lines, W and R- did not grow in soft agar. Cells were seeded at the indicated densities and colonies were counted after 25 days in culture. Numbers are averages of duplicate counts of a single experiment. Several assays were performed with reproducible results for each cell line. Several clones of (tsA) and (wtT) cells were also tested with similar results.

To exclude the possibility that the temperature-sensitive T antigen is somehow different from wild-type, additional lines were derived from the parental W and R- cells by co-transfecting two plasmids expressing wild-type SVLT and the hygromycin-resistance gene, respectively. Following hygromycin-selection, cells testing positive for T antigen expression were expanded into clones that were assayed for colony formation in soft agar. Again, in contrast to controls, the derivatives of R- cells were unable to form colonies, TABLE 5.

TABLE 6

GROWTH IN SOFT AGAR OF GLIOBLASTOMA CELL LINES
TREATED BY ANTISENSE STRATEGY TO THE IGF-1 RECEPTOR

| CELL TYPE | SEEDING DENSITY × $10^3$ | NUMBER OF COLONIES |
| --- | --- | --- |
| T98G-sense | 3 | 305 |
| T98G-antisense | 3 | 5 |
| C6 | 3 | 280 |
| C6-sense | 3 | 230 |
| C6-antisense | 3 | 115 |

Cells were seeded at the indicated densities and colonies were counted after 14 days in culture. Both cell lines showed a consistently higher efficiency of colony formation than t-antigen transfected mouse embryo cells. The T98G cells used are lines which have been stably transfected with a heat shock promoter construct which transcribes either a sense or antisense transcript for the first 309 bp of the IGF-1 receptor. The T98G cells containing the antisense construct grew at 40–50% of the rate of the lines containing the sense construct. The C6 cell line was treated with 80 µg/ml of antisense oligonucleotide to the IGF-1 receptor known to reduce the level of IGF-1 receptor at the cell surface (Pietrzkowski, et al., Cell Growth and Diff., 1992, 3:199). The sequence used corresponds to the first 18 bp after the ATG initiation codon of the IGF-1 receptor cDNA. the addition of the antisense oligonucleotide had very little effect on the anchorage dependent growth of these cells in 10% serum.

An additional experiment was performed to show that the ability of SVLT to transform fibroblasts depends directly on the presence of functional IGF-1 receptor. This experiment was based on the observation that cells expressing IGF-1 receptor constitutively are able to grow in serum-free medium supplemented with IGF-1 or insulin at supraphysiological concentrations (Pietrzkowski, et al., *Cell Growth and Diff.,* 1992, 3:199, McCubrey, et al., *Blood,* 1991, 78:921). Thus, one of the (tsA)R- clones was transfected with a plasmid (Cvn-IGF-1 receptor) expressing the full-length coding sequence of human Igflr cDNA and also the neomycin-resistance gene, both under the control of the SV40 promoter (Ullrich, et al., *EMBO J.* 1986, 5:2503). Clones selected directly in serum-free medium supplemented with insulin (20 µg/ml) were picked; under these conditions, only clones constitutively expressing the IGF-1 receptor can gown (Pietrzkowski, et al., supra). By autophosphorylation analysis, these clones expressed IGF-1 receptor at levels comparable to those of Balb/c 3T3 cells. these clones were able to form colonies efficiently in soft agar, without the addition of IGF-1. The endogenously-produced T antigen, which was previously ineffective, attained its transforming potential once the cells acquired constitutively-expressed human IGF-1 receptor.

Example 12

Immunostaining for Large T Antigen

Cells fixed in cold methanol were incubated with a 1:10 dilution of anti-large T antigen antibody (PAb 419; Oncogene Science, Uniondale, N.Y.) then stained with a 1:100 dilution of a fluorescinated goat antimouse immunoglobulin G antibody (Oncogene Science). Staining intensity was measured in arbitrary units by computer analysis of photographic images of the stained cells.

Example 13

Soft Agar Assay

Anchorage-independent growth was assayed by scoring the number of colonies formed in 0.2% agarose (with either a 1% or 0.4% agarose underlay). T antigen transfected cells were allowed to grow for three weeks while glioblastoma cell colonies were counted after two weeks due to the higher growth rate of these cells relative to the T antigen-transformed cells.

Previous indirect data, showing that NIH 3T3 cells over-expressing IGF-1 receptor grow in soft agar in the presence of the ligand (Kaleko, et al., *Mol. Cell. Biol.*, 1990, 10:464) and that the tumorigenicity of the rat glioblastoma C6 cell line is abrogated by antisense Igf-1 RNA (Trojan et al., supra) are consistent with the results obtained with mutant cells lacking IGF-1 receptor. These results suggest that IGF-1 receptor mediates signaling of IGF-1 is an indispensable component of the operation of a transformation pathway. To show that this is the case, an antisense RNA strategy was performed with C6 cells and also with cells of an additional glioblastoma cell line, T98G (Stein, supra), which grow well in 1% serum.

T98G glioblastoma cells were transfected with appropriate constructs, to derive cell lines expressing either antisense or (control) sense human Igflr RNA. Soft agar assays using these derivatives showed that, in comparison to the control cells, the number of colonies formed by 98G cells expressing Igflr antisense RNA was reduced more than 60-fold, see TABLE 6. In an analogous experiment, C6 cell colony formation in soft agar was reduced 2-fold in the presence of an antisense oligodeoxynucleotide inhibiting Iglfr mRNA, see TABLE 6. The growth of C6 cells in culture dishes was not reduced more than 10% in the presence of the same concentration of antisense oligodeoxynucleotides, while the growth rate of T98G cells expressing antisense RNA was 40% of that of wild-type cells or cells expressing sense RNA. These observations suggest that the transformation phenotype is more sensitive to the abrogation or diminution of IGF-1 receptor function than the inhibition of growth.

Example 14

Cross-Linking of IGF-1 Receptor

Radioiodinated IGF-1 was cross-linked to the IGF-1 receptor using disuccinimidyl suberate as described by Yamori, et al., *Cancer Res.,* 1991, 51, 5859. After cross-linking, the proteins were resolved on an 8% polyacrylamide gel and the dried gel exposed to X-ray film (Kodak X-OMAT) for autoradiography.

Example 15

Antisense Oligonucleotides

The antisense and sense oligodeoxynucleotides to the IGF-1 receptor mRNA used for the colony formation assay of C6 cells were prepared according to Pietrzkowski, et al., *Cell Growth and Diff.,* 1992, 3, 199. They correspond to the 18 bp sequence following the ATG of the IGF-1 receptor cDNA. The antisense oligonucleotides were added to the cells at the time of seeding at a concentration of 80 µg/ml.

Example 16

In vivo Experiments Performed in Rats

Three C6 cell lines were prepared. C6 cell lines were separately transfected with expression vectors capable of expressing sense or antisense oligonucleotides, respectively, to IGF-1 receptor RNA. Plasmids were prepared as described above. Wild type or untransfected C6 cells were also grown in culture. Cell lines were established by transfection of C6 with HSP70 promoter driving 305 bp of IGF-1 receptor RNA cell lines established by transfection. The cells carried a neomycin resistance gene. The cells were selected with G418 and monitored for IGF-1 receptor expression.

Rats were subcutaneously injected in the flank, i.e. side, with one of the three C6 rat glioblastoma cell lines at a concentration of $10^7$. This tumor grows vigorously in rats, reaching large sizes and eventually killing the animals. Rats injected with wild type cells resulted in tumors of about 1–2 cm.

Tumors results in rats injected with wild type cells and with cells expressing sense oligonucleotides, 27/27 rats injected with wild type cells and 12/12 rats injected with sense oligonucleotides, see TABLE 7. However, none of the 24 rats injected with antisense oligonucleotides yielded tumors, see TABLE 7.

In another experiment, animals were first injected with cells expressing sense oligonucleotides, prepared as set forth above, at a concentration of $10^7$. Six days later, the same animals were injected with wild type cells, at a concentration of $10^7$, and 6 of the 6 rats resulted in bilateral tumor development. None of the rats injected with antisense oligonucleotides initially and then wild type cells resulted in tumor development, see TABLE 7.

Another experiment injected wild type and sense expressing cells simultaneously, or wild type and antisense simultaneously. All of the rats given sense oligonucleotides (3/3) revealed tumors while 0/3 of the rate receiving antisense oligonucleotides had tumor development, see TABLE 7.

In anther experiment, fifteen rats were injected with wild type cells initially followed two weeks later with antisense oligonucleotides. Autopsies revealed (all injection concentrations were $10^7$ cells) complete tumor regression; the tumors disappeared. Significantly, the antisense oligonucleotides were injected into the flank opposite the wild type injection, TABLE 7.

TABLE 7

Effect of IGF-1R Sense and Antisense RNA on Tumor Induction in Rats

| Injection #1 (right) | Injection #2 (left) | Tumor Development number of animals |
|---|---|---|
| Wild - sense | n/a | 27/27 |
| Sense | n/a | 12/12 |
| Antisense | n/a | 0/24 |
| Sense | Wild-type (day 6) | 6/6 bilaterally |
| Antisense | Wild-type (day 6) | 0/6 |
| Wild-type | Sense (simultaneous) | 3/3 bilaterally |
| Wild-type | Antisense (simultaneous) | 0/3 |
| Wild-type | Antisense (2 weeks) | complete tumor regression in right flank, 15/15 |

The data resulting from the in vivo rat experiments identified above is significant for application to human cancers. The rat tumors in the above identified experiments were syngeneic. The tumors originated in these rats, the tumors are not foreign and the data is therefore the data is not the result of rejection of these tumors by the rats.

Various modifications of the invention in addition to those shown and described herein will be apparent to those skilled in the art from the foregoing description. Such modifications are also intended to fall within the scope of the appended claims.

What is claimed is:

1. A method of inhibiting proliferation of cancer cells in vivo comprising contacting said cancer cells in vivo with an effective amount of an oligonucleotide substantially complementary to a region of IGF-1 receptor RNA and which specifically hybridizes to IGF-1 receptor RNA.

2. The method of claim 1, wherein the oligonucleotide inhibits cancer cell proliferation in a soft agar assay.

3. The method of claim 1, wherein the oligonucleotide comprises a modified oligodeoxynucleotide.

4. The method of claim 3 wherein the modified oligodeoxynucleotide comprises at least one phosphorothioate linkage.

5. The method of claim 1, wherein the oligonucleotide is at least 18 nucleotides in length.

6. The method of claim 1, wherein the oligonucleotide is provided by an expression vector.

7. The method of claim 1, wherein the oligonucleotide is substantially complementary to the first 309 base pairs of the IGF-1 receptor coding region.

8. The method of claim 1 wherein the oligonucleotide is substantially complementary to the region of the IGF-1 receptor RNA that encodes a signal sequence.

9. The method of claim 5, wherein the oligonucleotide comprises the sequence SEQ ID NO:4.

10. The method of claim 3, wherein the oligonucleotide consists essentially of the sequence SEQ ID NO:4.

11. The method of claim 6, wherein the oligonucleotide is substantially complementary to the first 309 base pairs of the IGF-1 receptor coding region.

12. The method of claim 1, wherein the cancer cells are selected from the group consisting of prostate cancer cells, ovarian cancer cells, mammary cancer cells, lung cancer cells, and glioblastoma cells.

13. The method of claim 1 wherein the cancer cells are contacted with said oligonucleotide using a technique selected from the group consisting of liposome delivery, plasmid expression vector delivery, retroviral vector delivery, and delivery by subcutaneous injection.

14. A method of inducing regression of a tumor comprising contacting cells from the tumor in vivo with an effective amount of an oligonucleotide substantially complementary to a region of IGF-1 receptor RNA and which specifically hybridizes to IGF-1 receptor RNA.

15. The method of claim 14, wherein the oligonucleotide inhibits cancer cell proliferation in a soft agar assay.

16. The method of claim 14, wherein the oligonucleotide comprises a modified oligodeoxynucleotide.

17. The method of claim 16 wherein the modified oligodeoxynucleotide comprises at least one phosphorothioate linkage.

18. The method of claim 14 wherein the oligonucleotide is at least 18 nucleotides in length.

19. The method of claim 14 wherein the oligonucleotide is provided by an expression vector.

20. The method of claim 14 wherein the oligonucleotide is substantially complementary to the first 309 base pairs of the IGF-1 receptor coding region.

21. The method of claim 14, wherein the oligonucleotide is substantially complementary to the region of the IGF-1 receptor RNA that encodes a signal sequence.

22. The method of claim 18 wherein the oligonucleotide comprises the sequence SEQ ID NO:4.

23. The method of claim 16 wherein the oligonucleotide consists essentially of the sequence SEQ ID NO:4.

24. The method of claim 19 wherein the oligonucleotide is substantially complementary to the first 309 base pairs of the IGF-1 receptor coding region.

25. The method of claim 14 wherein the tumor cells are selected from the group consisting of prostate cancer cells, ovarian cancer cells, mammary cancer cells, lung cancer cells, and glioblastoma cells.

26. The method of claim 14 wherein the tumor cells are contacted with said oligonucleotide using a technique selected from the group consisting of liposome delivery, plasmid expression vector delivery, retroviral vector delivery, and delivery by subcutaneous injection.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:1:

ACCATTGATT CTGTTACTTC                                              20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

ATACTCTGTG ACATTCTTAA                                              20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

CTGCTCCTCT CCTAGGATGA                                              20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

TCCTCCGGAG CCAGACTT                                                18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

AAGTCTGGCT CCGGAGGA                                                18

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:6:

| GCACCGGGAA GTTGTGTCAA | 20 |
|---|---|

(2) INFORMATION FOR SEQ ID NO:7:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (xi) SEQUENCE DESCRIPTION: SEQ ID NO:7:

| CTTTGTTTTC TTTTCTTCCT CACAGACCTT CGGGCAAGGA CCTTCACAAG | 50 |
|---|---|
| GGATGCAGTA CATGCTCTGG CTGCCGTTGC GGATGAAGCC CGAGGGGCAC | 100 |
| TCCTGCATGC ACTCGCCGTC GTGGATCACA AACCCCTCGG AGTCGCTGCT | 150 |
| CTCGGCGCTG AGGATGTTGG CGCAGAAGTC ACGGTCCACA CAGCGCCAGC | 200 |
| CCTCAAACCT GTAGGTGTTG GCGGGCAGG CAGGCACACA GACACCGGCA | 250 |
| TAGTAGTAGT GGCGGCAAGC TACACAGGCC GTGTCGTTGT CAGGCGCGCT | 300 |
| GCAGCTGCCC AGGCACTCGG GGTGGCAGCA CTCATTGTTC TCGGTGCACG | 350 |
| CCCGCTTCCC ACACGTGCTT GGGCACATTT TCTGGCAGCG GTTTGTGGTC | 400 |
| CAGCAGCGGT AGTTGTACTC ATTGTTGATG GTGGTCTTCT CACACATCGG | 450 |
| CTTCTCCTCC ATGGTCCCTG GACACAGGTC CCCACATTCC TTTGGGGCT | 500 |
| TATTCCCCAC AATGTAGTTA TTGGACACCG CATCCAGGAT CAGGGACCAG | 550 |
| TCCACAGTGG AGAGGTAACA GAGGTCAGCA TTTTTCACAA TCCTGATGGC | 600 |
| CCCCGAGTA ATGTTCCTCA GGTTGTAAAG CCCAATATCC TTGAGATTGG | 650 |
| TCATCTCGAA GATGACCAGG GCGTAGTTGT AGAAGAGTTT CCAGCCGCGG | 700 |
| ATGACCGTGA GGTTGGGGAA GAGGTCTCCG AGGCTCTCGA GGCCAGCCAC | 750 |
| TCGGAACAGC AGCAAGTACT CGGTAATGAC CGTGAGCTTG GGGAAGCGGT | 800 |
| AGCTGCGGTA GTCCTCGGCC TTGGAGATGA GCAGGATGTG GAGGTAGCCC | 850 |
| TCGATCACCG TGCAGTTCTC CAGGCGCTTC AGCTGCTGAT AGTCGTTGCG | 900 |
| GATGTCGATG CCTGGCCCGC AGATTTC | 927 |

(2) INFORMATION FOR SEQ ID NO:8:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (xi) SEQUENCE DESCRIPTION: SEQ ID NO:8:

| CUUUGUUUUC UUUUCUUCCU CACAGACCUU CGGGCAAGGA CCUUCACAAG | 50 |
|---|---|
| GGAUGCAGUA CAUGCUCUGG CUGCCGUUGC GGAUGAAGCC CGAGGGGCAC | 100 |
| UCCUGCAUGC ACUCGCCGUC GUGGAUCACA AACCCCUCGG AGUCGCUGCU | 150 |
| CUCGGCGCUG AGGAUGUUGG CGCAGAAGUC ACGGUCCACA CAGCGCCAGC | 200 |
| CCUCAAACCU GUAGGUGUUG GCGGGCAGG CAGGCACACA GACACCGGCA | 250 |
| UAGUAGUAGU GGCGGCAAGC UACACAGGCC GUGUCGUUGU CAGGCGCGCU | 300 |
| GCAGCUGCCC AGGCACUCGG GGUGGCAGCA CUCAUUGUUC UCGGUGCACG | 350 |

```
CCCGCUUCCC ACACGUGCUU GGGCACAUUU UCUGGCAGCG GUUUGUGGUC         400

CAGCAGCGGU AGUUGUACUC AUUGUUGAUG GUGGUCUUCU CACACAUCGG         450

CUUCUCCUCC AUGGUCCCUG GACACAGGUC CCCACAUUCC UUUGGGGGCU         500

UAUUCCCCAC AAUGUAGUUA UUGGACACCG CAUCCAGGAU CAGGGACCAG         550

UCCACAGUGG AGAGGUAACA GAGGUCAGCA UUUUUCACAA UCCUGAUGGC         600

CCCCCGAGUA AUGUUCCUCA GGUUGUAAAG CCCAAUAUCC UUGAGAUUGG         650

UCAUCUCGAA GAUGACCAGG GCGUAGUUGU AGAAGAGUUU CCAGCCGCGG         700

AUGACCGUGA GGUUGGGGAA GAGGUCUCCG AGGCUCUCGA GGCCAGCCAC         750

UCGGAACAGC AGCAAGUACU CGGUAAUGAC CGUGAGCUUG GGGAAGCGGU         800

AGCUGCGGUA GUCCUCGGCC UUGGAGAUGA GCAGGAUGUG GAGGUAGCCC         850

UCGAUCACCU GCAGUUCUC CAGGCGCUUC AGCUGCUGAU AGUCGUUGCG          900

GAUGUCGAUG CCUGGCCCGC AGAUUUC                                  927

(2) INFORMATION FOR SEQ ID NO: 9:

(i) SEQUENCE CHARACTERISTICS:
        (A) LENGTH: 4989 base pairs
        (B) TYPE: nucleic acid
        (C) STRANDEDNESS: double
        (D) TOPOLOGY: linear (xi) SEQUENCE DESCRIPTION: SEQ ID NO: 9:

TTTTTTTTTT TTTTGAGAAA GGGAATTTCA TCCCAAATAA AAGGA ATG AAG TCT    54
                                                 Met Lys Ser
                                                  1

GGC TCC GGA GGA GGG TCC CCG ACC TCG CTG TGG GGG CTC CTG TTT     99
Gly Ser Gly Gly Gly Ser Pro Thr Ser Leu Trp Gly Leu Leu Phe
     5              10              15

CTC TCC GCC GCG CTC TCG CTC TGG CCG ACG AGT GGA GAA ATC TGC    144
Leu Ser Ala Ala Leu Ser Leu Trp Pro Thr Ser Gly Glu Ile Cys
 20              25              30

GGG CCA GGC ATC GAC ATC CGC AAC GAC TAT CAG CAG CTG AAG CGC    189
Gly Pro Gly Ile Asp Ile Arg Asn Asp Tyr Gln Gln Leu Lys Arg
     35              40              45

CTG GAG AAC TGC ACG GTG ATC GAG GGC TAC CTC CAC ATC CTG CTC    234
Leu Glu Asn Cys Thr Val Ile Glu Gly Tyr Leu His Ile Leu Leu
 50              55              60

ATC TCC AAG GCC GAG GAC TAC CGC AGC TAC CGC TTC CCC AAG CTC    279
Ile Ser Lys Ala Glu Asp Tyr Arg Ser Tyr Arg Phe Pro Lys Leu
 65              70              75

ACG GTC ATT ACC GAG TAC TTG CTG CTG TTC CGA GTG GCT GGC CTC    324
Thr Val Ile Thr Glu Tyr Leu Leu Leu Phe Arg Val Ala Gly Leu
 80              85              90

GAG AGC CTC GGA GAC CTC TTC CCC AAC CTC ACG GTC ATC CGC GGC    369
Glu Ser Leu Gly Asp Leu Phe Pro Asn Leu Thr Val Ile Arg Gly
 95              100             105

TGG AAA CTC TTC TAC AAC TAC GCC CTG GTC ATC TTC GAG ATG ACC    414
Trp Lys Leu Phe Tyr Asn Tyr Ala Leu Val Ile Phe Glu Met Thr
 110             115             120

AAT CTC AAG GAT ATT GGG CTT TAC AAC CTG AGG AAC ATT ACT CGG    459
Asn Leu Lys Asp Ile Gly Leu Tyr Asn Leu Arg Asn Ile Thr Arg
 125             130             135

GGG GCC ATC AGG ATT GAG AAA AAT GCT GAC CTC TGT TAC CTC TCC    504
Gly Ala Ile Arg Ile Glu Lys Asn Ala Asp Leu Cys Tyr Leu Ser
 140             145             150
```

```
ACT GTG GAC TGG TCC CTG ATC CTG GAT GCG GTG TCC AAT AAC TAC          549
Thr Val Asp Trp Ser Leu Ile Leu Asp Ala Val Ser Asn Asn Tyr
155                 160                 165

ATT GTG GGG AAT AAG CCC CCA AAG GAA TGT GGG GAC CTG TGT CCA          594
Ile Val Gly Asn Lys Pro Pro Lys Glu Cys Gly Asp Leu Cys Pro
    170                 175                 180

GGG ACC ATG GAG GAG AAG CCG ATG TGT GAG AAG ACC ACC ATC AAC          639
Gly Thr Met Glu Glu Lys Pro Met Cys Glu Lys Thr Thr Ile Asn
185                 190                 195

AAT GAG TAC AAC TAC CGC TGC TGG ACC ACA AAC CGC TGC CAG AAA          684
Asn Glu Tyr Asn Tyr Arg Cys Trp Thr Thr Asn Arg Cys Gln Lys
    200                 205                 210

ATG TGC CCA AGC ACG TGT GGG AAG CGG GCG TGC ACC GAG AAC AAT          729
Met Cys Pro Ser Thr Cys Gly Lys Arg Ala Cys Thr Glu Asn Asn
215                 220                 225

GAG TGC TGC CAC CCC GAG TGC CTG GGC AGC TGC AGC GCG CCT GAC          774
Glu Cys Cys His Pro Glu Cys Leu Gly Ser Cys Ser Ala Pro Asp
    230                 235                 240

AAC GAC ACG GCC TGT GTA GCT TGC CGC CAC TAC TAC TAT GCC GGT          819
Asn Asp Thr Ala Cys Val Ala Cys Arg His Tyr Tyr Tyr Ala Gly
245                 250                 255

GTC TGT GTG CCT GCC TGC CCG CCC AAC ACC TAC AGG TTT GAG GGC          864
Val Cys Val Pro Ala Cys Pro Pro Asn Thr Tyr Arg Phe Glu Gly
    260                 265                 270

TGG CGC TGT GTG GAC CGT GAC TTC TGC GCC AAC ATC CTC AGC GCC          909
Trp Arg Cys Val Asp Arg Asp Phe Cys Ala Asn Ile Leu Ser Ala
275                 280                 285

GAG AGC AGC GAC TCC GAG GGG TTT GTG ATC CAC GAC GGC GAG TGC          954
Glu Ser Ser Asp Ser Glu Gly Phe Val Ile His Asp Gly Glu Cys
    290                 295                 300

ATG CAG GAG TGC CCC TCG GGC TTC ATC CGC AAC GGC AGC CAG AGC          999
Met Gln Glu Cys Pro Ser Gly Phe Ile Arg Asn Gly Ser Gln Ser
305                 310                 315

ATG TAC TGC ATC CCT TGT GAA GGT CCT TGC CCG AAG GTC TGT GAG         1044
Met Tyr Cys Ile Pro Cys Glu Gly Pro Cys Pro Lys Val Cys Glu
    320                 325                 330

GAA GAA AAG AAA ACA AAG ACC ATT GAT TCT GTT ACT TCT GCT CAG         1089
Glu Glu Lys Lys Thr Lys Thr Ile Asp Ser Val Thr Ser Ala Gln
335                 340                 345

ATG CTC CAA GGA TGC ACC ATC TTC AAG GGC AAT TTG CTC ATT AAC         1134
Met Leu Gln Gly Cys Thr Ile Phe Lys Gly Asn Leu Leu Ile Asn
    350                 355                 360

ATC CGA CGG GGG AAT AAC ATT GCT TCA GAG CTG GAG AAC TTC ATG         1179
Ile Arg Arg Gly Asn Asn Ile Ala Ser Glu Leu Glu Asn Phe Met
365                 370                 375

GGG CTC ATC GAG GTG GTG ACG GGC TAC GTG AAG ATC CGC CAT TCT         1224
Gly Leu Ile Glu Val Val Thr Gly Tyr Val Lys Ile Arg His Ser
    380                 385                 390

CAT GCC TTG GTC TCC TTG TCC TTC CTA AAA AAC CTT CGC CTC ATC         1269
His Ala Leu Val Ser Leu Ser Phe Leu Lys Asn Leu Arg Leu Ile
395                 400                 405

CTA GGA GAG GAG CAG CTA GAA GGG AAT TAC TCC TTC TAC GTC CTC         1314
Leu Gly Glu Glu Gln Leu Glu Gly Asn Tyr Ser Phe Tyr Val Leu
    410                 415                 420

GAC AAC CAG AAC TTG CAG CAA CTG TGG GAC TGG GAC CAC CGC AAC         1359
Asp Asn Gln Asn Leu Gln Gln Leu Trp Asp Trp Asp His Arg Asn
425                 430                 435

CTG ACC ATC AAA GCA GGG AAA ATG TAC TTT GCT TTC AAT CCC AAA         1404
Leu Thr Ile Lys Ala Gly Lys Met Tyr Phe Ala Phe Asn Pro Lys
```

```
                -continued 440                   445                   450
TTA TGT GTT TCC GAA ATT TAC CGC ATG GAG GAA GTG ACG GGG ACT            1449
Leu Cys Val Ser Glu Ile Tyr Arg Met Glu Glu Val Thr Gly Thr
    455                   460                   465

AAA GGG CGC CAA AGC AAA GGG GAC ATA AAC ACC AGG AAC AAC GGG            1494
Lys Gly Arg Gln Ser Lys Gly Asp Ile Asn Thr Arg Asn Asn Gly
    470                   475                   480

GAG AGA GCC TCC TGT GAA AGT GAC GTC CTG CAT TTC ACC TCC ACC            1539
Glu Arg Ala Ser Cys Glu Ser Asp Val Leu His Phe Thr Ser Thr
    485                   490                   495

ACC ACG TCG AAG AAT CGC ATC ATC ATA ACC TGG CAC CGG TAC CGG            1584
Thr Thr Ser Lys Asn Arg Ile Ile Ile Thr Trp His Arg Tyr Arg
    500                   505                   510

CCC CCT GAC TAC AGG GAT CTC ATC AGC TTC ACC GTT TAC TAC AAG            1629
Pro Pro Asp Tyr Arg Asp Leu Ile Ser Phe Thr Val Tyr Tyr Lys
    515                   520                   525

GAA GCA CCC TTT AAG AAT GTC ACA GAG TAT GAT GGG CAG GAT GCC            1674
Glu Ala Pro Phe Lys Asn Val Thr Glu Tyr Asp Gly Gln Asp Ala
    530                   535                   540

TGC GGC TCC AAC AGC TGG AAC ATG GTG GAC GTG GAC CTC CCG CCC            1719
Cys Gly Ser Asn Ser Trp Asn Met Val Asp Val Asp Leu Pro Pro
    545                   550                   555

AAC AAG GAC GTG GAG CCC GGC ATC TTA CTA CAT GGG CTG AAG CCC            1764
Asn Lys Asp Val Glu Pro Gly Ile Leu Leu His Gly Leu Lys Pro
    560                   565                   570

TGG ACT CAG TAC GCC GTT TAC GTC AAG GCT GTG ACC CTC ACC ATG            1809
Trp Thr Gln Tyr Ala Val Tyr Val Lys Ala Val Thr Leu Thr Met
    575                   580                   585

GTG GAG AAC GAC CAT ATC CGT GGG GCC AAG AGT GAG ATC TTG TAC            1854
Val Glu Asn Asp His Ile Arg Gly Ala Lys Ser Glu Ile Leu Tyr
    590                   595                   600

ATT CGC ACC AAT GCT TCA GTT CCT TCC ATT CCC TTG GAC GTT CTT            1899
Ile Arg Thr Asn Ala Ser Val Pro Ser Ile Pro Leu Asp Val Leu
    605                   610                   615

TCA GCA TCG AAC TCC TCT TCT CAG TTA ATC GTG AAG TGG AAC CCT            1944
Ser Ala Ser Asn Ser Ser Ser Gln Leu Ile Val Lys Trp Asn Pro
    620                   625                   630

CCC TCT CTG CCC AAC GGC AAC CTG AGT TAC TAC ATT GTG CGC TGG            1989
Pro Ser Leu Pro Asn Gly Asn Leu Ser Tyr Tyr Ile Val Arg Trp
    635                   640                   645

CAG CGG CAG CCT CAG GAC GGC TAC CTT TAC CGG CAC AAT TAC TGC            2034
Gln Arg Gln Pro Gln Asp Gly Tyr Leu Tyr Arg His Asn Tyr Cys
    650                   655                   660

TCC AAA GAC AAA ATC CCC ATC AGG AAG TAT GCC GAC GGC ACC ATC            2079
Ser Lys Asp Lys Ile Pro Ile Arg Lys Tyr Ala Asp Gly Thr Ile
    665                   670                   675

GAC ATT GAG GAG GTC ACA GAG AAC CCC AAG ACT GAG GTG TGT GGT            2124
Asp Ile Glu Glu Val Thr Glu Asn Pro Lys Thr Glu Val Cys Gly
    680                   685                   690

GGG GAG AAA GGG CCT TGC TGC GCC TGC CCC AAA ACT GAA GCC GAG            2169
Gly Glu Lys Gly Pro Cys Cys Ala Cys Pro Lys Thr Glu Ala Glu
    695                   700                   705

AAG CAG GCC GAG AAG GAG GAG GCT GAA TAC CGC AAA GTC TTT GAG            2214
Lys Gln Ala Glu Lys Glu Glu Ala Glu Tyr Arg Lys Val Phe Glu
    710                   715                   720

AAT TTC CTG CAC AAC TCC ATC TTC GTG CCC AGA CCT GAA AGG AAG            2259
Asn Phe Leu His Asn Ser Ile Phe Val Pro Arg Pro Glu Arg Lys
    725                   730                   735

CGG AGA GAT GTC ATG CAA GTG GCC AAC ACC ACC ATG TCC AGC CGA            2304
```

-continued

```
                Arg Arg Asp Val Met Gln Val Ala Asn Thr Thr Met Ser Ser Arg
                740                 745                 750

AGC AGG AAC ACC ACG GCC GCA GAC ACC TAC AAC ATC ACC GAC CCG              2349
Ser Arg Asn Thr Thr Ala Ala Asp Thr Tyr Asn Ile Thr Asp Pro
755                 760                 765

GAA GAG CTG GAG ACA GAG TAC CCT TTC TTT GAG AGC AGA GTG GAT              2394
Glu Glu Leu Glu Thr Glu Tyr Pro Phe Phe Glu Ser Arg Val Asp
770                 775                 780

AAC AAG GAG AGA ACT GTC ATT TCT AAC CTT CGG CCT TTC ACA TTG              2439
Asn Lys Glu Arg Thr Val Ile Ser Asn Leu Arg Pro Phe Thr Leu
785                 790                 795

TAC CGC ATC GAT ATC CAC AGC TGC AAC CAC GAG GCT GAG AAG CTG              2484
Tyr Arg Ile Asp Ile His Ser Cys Asn His Glu Ala Glu Lys Leu
800                 805                 810

GGC TGC AGC GCC TCC AAC TTC GTC TTT GCA AGG ACT ATG CCC GCA              2529
Gly Cys Ser Ala Ser Asn Phe Val Phe Ala Arg Thr Met Pro Ala
815                 820                 825

GAA GGA GCA GAT GAC ATT CCT GGG CCA GTG ACC TGG GAG CCA AGG              2574
Glu Gly Ala Asp Asp Ile Pro Gly Pro Val Thr Trp Glu Pro Arg
830                 835                 840

CCT GAA AAC TCC ATC TTT TTA AAG TGG CCG GAA CCT GAG AAT CCC              2619
Pro Glu Asn Ser Ile Phe Leu Lys Trp Pro Glu Pro Glu Asn Pro
845                 850                 855

AAT GGA TTG ATT CTA ATG TAT GAA ATA AAA TAC GGA TCA CAA GTT              2664
Asn Gly Leu Ile Leu Met Tyr Glu Ile Lys Tyr Gly Ser Gln Val
860                 865                 870

GAG GAT CAG CGA GAA TGT GTG TCC AGA CAG GAA TAC AGG AAG TAT              2709
Glu Asp Gln Arg Glu Cys Val Ser Arg Gln Glu Tyr Arg Lys Tyr
875                 880                 885

GGA GGG GCC AAG CTA AAC CGG CTA AAC CCG GGG AAC TAC ACA GCC              2754
Gly Gly Ala Lys Leu Asn Arg Leu Asn Pro Gly Asn Tyr Thr Ala
890                 895                 900

CGG ATT CAG GCC ACA TCT CTC TCT GGG AAT GGG TCG TGG ACA GAT              2799
Arg Ile Gln Ala Thr Ser Leu Ser Gly Asn Gly Ser Trp Thr Asp
905                 910                 915

CCT GTG TTC TTC TAT GTC CAG GCC AAA ACA GGA TAT GAA AAC TTC              2844
Pro Val Phe Phe Tyr Val Gln Ala Lys Thr Gly Tyr Glu Asn Phe
920                 925                 930

ATC CAT CTG ATC ATC GCT CTG CCC GTC GCT GTC CTG TTG ATC GTG              2889
Ile His Leu Ile Ile Ala Leu Pro Val Ala Val Leu Leu Ile Val
935                 940                 945

GGA GGG TTG GTG ATT ATG CTG TAC GTC TTC CAT AGA AAG AGA AAT              2934
Gly Gly Leu Val Ile Met Leu Tyr Val Phe His Arg Lys Arg Asn
950                 955                 960

AAC AGC AGG CTG GGG AAT GGA GTG CTG TAT GCC TCT GTG AAC CCG              2979
Asn Ser Arg Leu Gly Asn Gly Val Leu Tyr Ala Ser Val Asn Pro
965                 970                 975

GAG TAC TTC AGC GCT GCT GAT GTG TAC GTT CCT GAT GAG TGG GAG              3024
Glu Tyr Phe Ser Ala Ala Asp Val Tyr Val Pro Asp Glu Trp Glu
980                 985                 990

GTG GCT CGG GAG AAG ATC ACC ATG AGC CGG GAA CTT GGG CAG GGG              3069
Val Ala Arg Glu Lys Ile Thr Met Ser Arg Glu Leu Gly Gln Gly
995                 1000                1005

TCG TTT GGG ATG GTC TAT GAA GGA GTT GCC AAG GGT GTG GTG AAA              3114
Ser Phe Gly Met Val Tyr Glu Gly Val Ala Lys Gly Val Val Lys
1010                1015                1020

GAT GAA CCT GAA ACC AGA GTG GCC ATT AAA ACA GTG AAC GAG GCC              3159
Asp Glu Pro Glu Thr Arg Val Ala Ile Lys Thr Val Asn Glu Ala
1025                1030                1035
```

```
GCA AGC ATG CGT GAG AGG ATT GAG TTT CTC AAC GAA GCT TCT GTG        3204
Ala Ser Met Arg Glu Arg Ile Glu Phe Leu Asn Glu Ala Ser Val
    1040                1045                1050

ATG AAG GAG TTC AAT TGT CAC CAT GTG GTG CGA TTG CTG GGT GTG        3249
Met Lys Glu Phe Asn Cys His His Val Val Arg Leu Leu Gly Val
    1055                1060                1065

GTG TCC CAA GGC CAG CCA ACA CTG GTC ATC ATG GAA CTG ATG ACA        3294
Val Ser Gln Gly Gln Pro Thr Leu Val Ile Met Glu Leu Met Thr
    1070                1075                1080

CGG GGC GAT CTC AAA AGT TAT CTC CGG TCT CTG AGG CCA GAA ATG        3339
Arg Gly Asp Leu Lys Ser Tyr Leu Arg Ser Leu Arg Pro Glu Met
    1085                1090                1095

GAG AAT AAT CCA GTC CTA GCA CCT CCA AGC CTG AGC AAG ATG ATT        3384
Glu Asn Asn Pro Val Leu Ala Pro Pro Ser Leu Ser Lys Met Ile
    1100                1105                1110

CAG ATG GGC GGA GAG ATT GCA GAC GGC ATG GCA TAC CTC AAC GCC        3429
Gln Met Ala Gly Glu Ile Ala Asp Gly Met Ala Tyr Leu Asn Ala
    1115                1120                1125

AAT AAG TTC GTC CAC AGA GAC CTT GCT GCC CGG AAT TGC ATG GTA        3474
Asn Lys Phe Val His Arg Asp Leu Ala Ala Arg Asn Cys Met Val
    1130                1135                1140

GCC GAA GAT TTC ACA GTC AAA ATC GGA GAT TTT GGT ATG ACG CGA        3519
Ala Glu Asp Phe Thr Val Lys Ile Gly Asp Phe Gly Met Thr Arg
    1145                1150                1155

GAT ATC TAT GAG ACA GAC TAT TAC CGG AAA GGA GGG AAA GGG CTG        3564
Asp Ile Tyr Glu Thr Asp Tyr Tyr Arg Lys Gly Gly Lys Gly Leu
    1160                1165                1170

CTG CCC GTG CGC TGG ATG TCT CCT GAG TCC CTC AAG GAT GGA GTC        3609
Leu Pro Val Arg Trp Met Ser Pro Glu Ser Leu Lys Asp Gly Val
    1175                1180                1185

TTC ACC ACT TAC TCG GAC GTC TGG TCC TTC GGG GTC GTC CTC TGG        3654
Phe Thr Thr Tyr Ser Asp Val Trp Ser Phe Gly Val Val Leu Trp
    1190                1195                1200

GAG ATC GCC ACA CTG GCC GAG CAG CCC TAC CAG GGC TTG TCC AAC        3699
Glu Ile Ala Thr Leu Ala Glu Gln Pro Tyr Gln Gly Leu Ser Asn
    1205                1210                1215

GAG CAA GTC CTT CGC TTC GTC ATG GAG GGC GGC CTT CTG GAC AAG        3744
Glu Gln Val Leu Arg Phe Val Met Glu Gly Gly Leu Leu Asp Lys
    1220                1225                1230

CCA GAC AAC TGT CCT GAC ATG CTG TTT GAA CTG ATG CGC ATG TGC        3789
Pro Asp Asn Cys Pro Asp Met Leu Phe Glu Leu Met Arg Met Cys
    1235                1240                1245

TGG CAG TAT AAC CCC AAG ATG AGG CCT TCC TTC CTG GAG ATC ATC        3834
Trp Gln Tyr Asn Pro Lys Met Arg Pro Ser Phe Leu Glu Ile Ile
    1250                1255                1260

AGC AGC ATC AAA GAG GAG ATG GAG CCT GGC TTC CGG GAG GTC TCC        3879
Ser Ser Ile Lys Glu Glu Met Glu Pro Gly Phe Arg Glu Val Ser
    1265                1270                1275

TTC TAC TAC AGC GAG GAG AAC AAG CTG CCC GAG CCG GAG GAG CTG        3924
Phe Tyr Tyr Ser Glu Glu Asn Lys Leu Pro Glu Pro Glu Glu Leu
    1280                1285                1290

GAC CTG GAG CCA GAG AAC ATG GAG AGC GTC CCC CTG GAC CCC TCG        3969
Asp Leu Glu Pro Glu Asn Met Glu Ser Val Pro Leu Asp Pro Ser
    1295                1300                1305

GCC TCC TCG TCC TCC CTG CCA CTG CCC GAC AGA CAC TCA GGA CAC        4014
Ala Ser Ser Ser Ser Leu Pro Leu Pro Asp Arg His Ser Gly His
    1310                1315                1320

AAG GCC GAG AAC GGC CCC GGC CCT GGG GTG CTG GTC CTC CGC GCC        4059
Lys Ala Glu Asn Gly Pro Gly Pro Gly Val Leu Val Leu Arg Ala
    1325                1330                1335
```

```
AGC TTC GAC GAG AGA CAG CCT TAC GCC CAC ATG AAC GGG GGC CGC          4104
Ser Phe Asp Glu Arg Gln Pro Tyr Ala His Met Asn Gly Gly Arg
    1340                1345                1350

AAG AAC GAG CGG GCC TTG CCG CTG CCC CAG TCT TCG ACC TGC TGA          4149
Lys Asn Glu Arg Ala Leu Pro Leu Pro Gln Ser Ser Thr Cys
    1355                1360                1365

TCCTTGGATC CTGAATCTGT GCAAACAGTA ACGTGTGCGC ACGCGCAGCG GGGTGGGGGG    4209

GGAGAGAGAG TTTTAACAAT CCATTCACAA GCCTCCTGTA CCTCAGTGGA TCTTCAGTTC    4269

TGCCCTTGCT GCCCGCGGGA GACAGCTTCT CTGCAGTAAA ACACATTTGG GATGTTCCTT    4329

TTTTCAATAT GCAAGCAGCT TTTTATTCCC TGCCCAAACC CTTAACTGAC ATGGGCCTTT    4389

AAGAACCTTA ATGACAACAC TTAATAGCAA CAGAGCACTT GAGAACCAGT CTCCTCACTC    4449

TGTCCCTGTC CTTCCCTGTT CTCCCTTTCT CTCTCCTCTC TGCTTCATAA CGGAAAAATA    4509

ATTGCCACAA GTCCAGCTGG GAAGCCCTTT TTATCAGTTT GAGGAAGTGG CTGTCCCTGT    4569

GGCCCCATCC CACCACTGTA CACACCCGCC TGACACCGTG GGTCATTACA AAAAAACACG    4629

TGGAGATGGA AATTTTTACC TTTATCTTTC ACCTTTCTAG GGACATGAAA TTTACAAAGG    4689

GCCATCGTTC ATCCAAGGCT GTTACCATTT TAACGCTGCC TAATTTTGCC AAAATCCTGA    4749

ACTTTCTCCC TCATCGGCCC GGCGCTGATT CCTCGTGTCC GGAGGCATGG GTGAGCATGG    4809

CAGCTGGTTG CTCCATTTGA GAGACACGCT GGCGACACAC TCCGTCCATC CGACTGCCCC    4869

TGCTGTGCTG CTCAAGGCCA CAGGCACACA GGTCTCAATG CTTCTGACTA GATTATTATT    4929

TGGGGGAACT GGACACAATA GGTCTTTCTC TCAGTGAAGG TGGGGAGAAG CTGAACCGGC    4989
```